(12) United States Patent
Chen et al.

(10) Patent No.: US 9,517,202 B2
(45) Date of Patent: Dec. 13, 2016

(54) PHOSPHOLIPID DEPOT

(75) Inventors: Andrew Xian Chen, San Diego, CA (US); Hailiang Chen, San Diego, CA (US)

(73) Assignee: LATITUDE PHARMACEUTICALS INC., San Diego, CA (US)

( * ) Notice: Subject to any disclaimer, the term of this patent is extended or adjusted under 35 U.S.C. 154(b) by 0 days.

(21) Appl. No.: 13/523,860

(22) Filed: Jun. 14, 2012

(65) Prior Publication Data

US 2012/0316108 A1 Dec. 13, 2012

Related U.S. Application Data

(63) Continuation of application No. PCT/US2010/060964, filed on Dec. 17, 2010.

(60) Provisional application No. 61/288,220, filed on Dec. 18, 2009.

(51) Int. Cl.

| A61K 47/24 | (2006.01) |
| A61K 38/02 | (2006.01) |
| A61K 38/28 | (2006.01) |
| A61K 47/44 | (2006.01) |
| A61K 47/28 | (2006.01) |
| A61K 47/26 | (2006.01) |
| A61K 47/36 | (2006.01) |
| A61K 31/661 | (2006.01) |
| A61P 3/10 | (2006.01) |
| A61P 17/00 | (2006.01) |
| A61K 9/06 | (2006.01) |
| A61K 9/00 | (2006.01) |

(52) U.S. Cl.
CPC .............. *A61K 9/06* (2013.01); *A61K 9/0019* (2013.01); *A61K 38/28* (2013.01); *A61K 47/24* (2013.01)

(58) Field of Classification Search
CPC ...... A61K 38/28; A61K 47/24; A61K 9/0019; A61K 9/06
See application file for complete search history.

(56) References Cited

U.S. PATENT DOCUMENTS

| 4,708,861 A | * | 11/1987 | Popescu et al. | 424/1.21 |
| 4,963,526 A | * | 10/1990 | Ecanow | 424/456 |
| 5,498,420 A | * | 3/1996 | Mentrup Edgar et al. | 424/450 |
| 5,576,016 A | * | 11/1996 | Amselem et al. | 424/450 |
| 5,711,965 A | * | 1/1998 | Ghyczy et al. | 424/450 |
| 2005/0118206 A1 | * | 6/2005 | Luk et al. | 424/400 |
| 2005/0287180 A1 | * | 12/2005 | Chen | 424/400 |
| 2006/0039978 A1 | * | 2/2006 | Diederichs | 424/484 |
| 2006/0228405 A1 | * | 10/2006 | Ulm et al. | 424/450 |
| 2006/0286161 A1 | * | 12/2006 | Panzner et al. | 424/450 |

FOREIGN PATENT DOCUMENTS

| EP | 2 210 589 A1 | 7/2010 | | |
| WO | 03/059280 A2 | 7/2003 | | |
| WO | 2004/047790 A2 | 6/2004 | | |
| WO | 2007/110767 A2 | 10/2007 | | |
| WO | WO 2009067734 A1 | * | 6/2009 | A61K 47/44 |

OTHER PUBLICATIONS

Jui-Yoa Chang, Stability of Hirudin, a Thrombin-specific Inhibitor, The Journal of Biological Chemistry, vol. 266, No. 17, Issue of Jun. 15, pp. 10839-10843, 1991.*
International Search Report of PCT/US2010/060964 mailed Feb. 25, 2011.

* cited by examiner

*Primary Examiner* — James H Alstrum Acevedo
*Assistant Examiner* — Erinne Dabkowski
(74) *Attorney, Agent, or Firm* — Kilpatrick Townsend & Stockton LLP

(57) ABSTRACT

The present invention is directed to phospholipid compositions and methods of preparation of phospholipid depots that are injectable through a fine needle. The phospholipid depots prepared by the methods described herein comprise nanometer-sized phospholipid particles and exhibit a higher degree of structural order compared to compositions prepared by other methods.

14 Claims, 10 Drawing Sheets

PHOSPHOLIPID DEPOT

CROSS-REFERENCES TO RELATED APPLICATIONS

The present application is a continuation of PCT/US2010/060964, filed Dec. 17, 2010, which application claims priority to U.S. Provisional Patent Application No. 61/288,220, filed Dec. 18, 2009, the teachings of which are hereby incorporated by reference in their entirety for all purposes.

FIELD OF THE INVENTION

The present invention relates to phospholipid depot compositions for insulin and other drugs and methods for preparation.

BACKGROUND OF THE INVENTION

An injectable depot is designed to prolong the duration of action and reduce the frequency of injection for a drug. Such depots are generally administered by subcutaneous or intramuscular injection or by injection or instillation into body tissues, vessels or cavities. A depot prolongs the action of a pharmacologically active agent by releasing it into surrounding tissues from a reservoir slowly over time. A 1-day, 7-day or 30-day depot release profile, which enables a once-a-day, once-a-week or once-a-month injection schedule, respectively, would be highly desirable for convenience and better patient compliance.

Various materials have been employed for depot compositions. The most common depot-forming materials are biodegradable synthetic polymers, e.g., polylactic-co-glycolic acid (PLGA) and polylactic acid (PLA). The biodegradable polymer depot generally comes in two common forms: microcapsules/microspheres and polymer gels. The PLGA/PLA depots have been used in several FDA approved drugs i.e., Zoladex™ (goserelin acetate) and Lupron Depot™ (leuprolide acetate), which are PLGA microcapsules and microsphere, respectively. Eligard™ is in a polymer gel made by dissolving a drug and PLGA in a strong organic solvent i.e., N-methyl-2-pyrrolidone.

A major disadvantage of the polymer depots is that they require large diameter needles for injection or implantation due to the physical size of the microcapsules/microspheres and/or the high viscosity of the polymer gel. For example, 14- or 16-gauge (G) needles are required for implantation of Zoladex™ and 18 G or 20 G needles for injection of Eligard™. However, in common medical practice, needles of size greater than 21 G are generally not used for injection because they cause significant pain and psychological trauma for patients. For drugs like insulin, which are self-administered daily, fine 25-27 G needles and 1 cc syringes are used. The injectability or ease with which the end user can self-inject through such a system will be key to such a drug's user compliance and therapeutic efficacy. For discussion purposes herein, the injectability of a syringe-administered depot is quantitatively defined as meeting the "Acceptable Injectability Criterion" if it requires an applied force of no more than 10 pounds to be extruded from a 1 cc syringe through a 25 G ½ inch long needle at rate of 2 cc/min. Such a scenario represents typical conditions during the self-administration of insulin and other self-injected drugs.

Moreover, PLGA and PLA are insoluble in water and both require extremely strong organic solvents such as methylene chloride, chloroform or N-methyl-2-pyrrolidone to fabricate the microcapsules/microspheres or gels. Unfortunately, most biological molecules such as protein drugs are incompatible with strong solvents. Methylene chloride or N-methyl-2-pyrrolidone, which are used in PLGA/PLA production, denature insulin immediately upon contact.

Phospholipids (PL) are naturally occurring substances in the human body and are the major constituents of cell membranes. These molecules have an established record of safety and biocompatibility as components in injected medicines. PL are also generally insoluble in water (like the PLGA polymers) and following injection into tissue and coming into contact with aqueous body fluids and tissues, PL can precipitate and trap a co-administered drug, to form a drug-PL co-precipitate that can function as a depot. Over time, this mass diffuses slowly into a surrounding tissue and/or is degraded by phospholipase, which is an enzyme distributed throughout the body that slowly hydrolyzes phospholipids, resulting in a slow release of the trapped drug. With such favorable safety, solubility and biocompatibility properties, it would appear that phospholipids are ideal depot materials. However, to date, there has been few successful depot drug product based on phospholipids. One primary problem is the poor injectability associated with phospholipid-based compositions.

This inventor has discovered that a high concentration (i.e., 20-80%) of phospholipids is generally required in order to form the mass that permits depot functionality. However, once the phospholipid concentration exceeds about 20% in a composition, the composition becomes thick, viscous and difficult to inject through fine needles without using an excessively high force. For example, Phosal 50PG, Phosal 50SA, and Phosal 50MCT (produced by the America Lecithin Company) are liposome-forming compositions containing about 50% phospholipids dissolved in propylene glycol/ethanol, oil, and medium chain oil, respectively. With their honey-like consistency, the Phosal compositions are very difficult to inject using a conventional hypodermic needle and syringe. It requires more than 20 pounds of force to extrude Phosal through a 25 G ½ inch long needle from a 1 cc syringe at a plunger speed of 2 cc/min. Thus, it will take 2-5 minutes or more to manually extrude 1 mL of the Phosal-based depot through a 26 G needle even using a very high force—which is impractical for general medical use and definitely not suitable for self-administration. Therefore, acceptable injectability using fine hyperdermic needles has been a main reason preventing phospholipids from becoming useful depot materials. This invention discloses phospholipid depots with surprisingly good injectability that meets the Acceptable Injectability Criterion, as defined above.

Another difficulty working with phospholipids is that phospholipids are only soluble in certain organic solvents (e.g., ethanol) or oil (e.g., vegetable oil) and many drugs (such as insulin or other protein drugs) are only soluble and stable in water, but not soluble or stable in solvents or oils that can dissolve phospholipids. Therefore, it has been impossible to manufacture phospholipid-based depots using conventional solvent methods or other methods disclosed in prior art without having the solvent-sensitive drugs precipitate or degrade (See WO 2006/002050, U.S. Pat. No. 5,807,573, WO/1994/008623, U.S. Pat. No. 5,004,611 and Harry Tiemesseen, et al. (2004) European Journal of Pharmaceutics and Biopharmaceutics Volume 58 (2005), pp 587-593).

Another hurdle in the production of phospholipid depots relates to difficulty in preparing a depot suitable for injection under sterile conditions. Many drugs are heat-sensitive and cannot survive heat sterilization (e.g., autoclaving) or radiation sterilization. This is especially true for biological drugs such as insulin and other protein drugs. In many cases, the only practical way to sterilize a protein-containing composition is by filtration through a 0.2- or 0.45-micron pore membrane to remove any microbial contaminants. With a 20-80% phospholipid content, the thick consistency of the depot compositions precludes any possibility of sterilization by filtration. Therefore, this invention also teaches unique methods for preparing depots that may be sterilized by filtration.

Insulin is the mainstay for treatment of virtually all type 1 and many type 2 diabetic patients. Insulins and insulin formulations are divided into two types: (1) quick onset/short acting and (2) long-acting. The first type ("preprandial") is used to control transient elevated blood glucose levels that occur after meals. Long-acting insulin is used to maintain a controlled baseline level of glucose level over a long duration such as 12-24 hours. A long-acting insulin or insulin formulation is thus referred to as "basal insulin."

Basal insulin therapy is utilized to achieve "glycemic control," which is the maintenance of blood glucose levels at a constant and acceptable level without fluctuations. Sufficient glycemic control requires plasma glucose levels to be maintained within normal limits (70-130 mg/dl, or 3.9-7.2 mmol/L) and indistinguishable from that in a non-diabetic person. Glucose level fluctuations, especially the high peaks and valleys resulting from poor glycemic control, are high risk factors for diabetes-associated complications that can lead to morbidity and mortality. Therefore, to achieve adequate glycemic control, an ideal basal insulin formulation should deliver insulin to the circulation at a constant rate (i.e., peak-less) over a prolonged period of time, such as 24 hours. Human insulin itself has a rapid onset and short duration of action (the half-life of insulin is only about 5-6 minutes in the circulation). Therefore, a human insulin depot formulation requires an approach that is capable of both sequestering and releasing it slowly and constantly to address the requirements needed for a successful basal insulin therapy.

The pharmacological efficacy of insulin can be readily monitored by following the post-administration plasma glucose concentration-time profile and the plasma insulin concentration-time profile. The former measures insulin's glucose-lowering efficacy or the pharmacodynamic or PD profile and the latter measures the insulin plasma levels as a pharmacokinetic or PK profile.

The currently available basal human insulin formulations in the US include the NPH (Neutral Protamine Hagedorn) insulin sold under the trade names of HUMULIN® N and NOVOLIN® N by Eli Lilly and Company and Novo Nordisk, respectively. NPH insulin, which was invented in the 1930's by Hans Christian Hagedorn, is a suspension of zinc-insulin crystalline complexes combined with the positively charged polypeptide, protamine. The complexation with zinc and protamine turns the insulin into insoluble particles after injection that slowly release insulin.

Despite its long history of use (over 70 years), NPH is not an ideal depot formulation for basal insulin therapy. The following shortcomings are well known:

High $C_{max}$: The NPH PK profile has a pronounced peak or $C_{max}$ that occurs in about 4 hours after subcutaneous injection. This high $C_{max}$ causes hypoglcermia. Since basal insulin is typically given at bedtime, the 4 hr post-injection hypoglycemic phase normally occurs when the patient is asleep. However, if the patient were to awaken in the middle of the night and get out of bed, the hypoglycemic episode could lead to fainting.

Short duration of action: NPH releases a substantial amount of its insulin within the first few hours and is depleted in about 14-16 hours, making it suitable only as a twice-a-day (BID) formulation. This deficiency disqualifies NPH as a true, once-a-day (QD) formulation.

High peak-to-valley ratio of plasma insulin: In clinical practice, BID regimens for NPH are still unable to stem high $C_{max}$ (peak) and low $C_{min}$ (valley) fluctuations. The resulting sub-optimal glycemic control increases the risk for diabetic complications.

Poor dose uniformity: For suspensions like NPH, an intrinsic problem is the inability to achieve uniform injection-to-injection dosing in a small volumes—even with strict adherence to the rigorous pre-injection mixing/shaking instructions. For NPH this difficulty is further compounded because it is typically injected in very small volumes (<1 mL). Thus, the variability with respect to the amount of insulin injected dose-to-dose for NPH can be as high as 10-20%, which also contributes to poor glycemic control.

More recently, two basal insulin drugs, LANTUS® (insulin glargine, Sanofi-aventis) and LEVEMIR® (insulin detemir, Novo Nordisk), were developed and subsequently approved. Both LANTUS® and LEVEMIR® are insulin analogs, in that they are chemically modified insulin and are not the authentic human insulin molecule. In contrast to NPH, LANTUS® releases insulin in a "peak-less" (peak to trough ratio less than 5 within 24 hours after each injection) PK profile over 24 hours, which are key factors underlying the drug's applicability as a once-a-day dose and its achievement of better glycemic control. Compared to NPH, LEVEMIR® has a less spiky PK profile but its duration of action is somewhat similar to NPH, making it suitable only for BID dosing. Of these two basal insulin analogs, LANTUS® has clear advantages over NPH owing to its 24 hr peak-less insulin PK profile.

Recently, LANTUS® has been reportedly linked to certain cancers. The FDA noted: "3 of 4 observational studies suggest an increased risk for cancer associated with use of LANTUS®." (Pink Sheet, Jul. 6, 2009, p. 30). LANTUS® is also associated with a high incidence of injection site pain possibly due to its low pH formulation (pH 4). Unlike human insulin, the long-term safety of the insulin analogs are unclear.

Despite the recent advances for insulin drugs, there is a need for improved basal insulin formulations that provide a 24 hr peak-less PK profile. Moreover, there remains a need for a phospholipid depot suitable for injection under sterile conditions. A method is needed to enable a water-soluble or solvent-incompatible drug to be incorporated into a phospholipid depot. The present invention satisfies these and other needs.

BRIEF SUMMARY OF THE INVENTION

The present invention provides compositions and methods for preparing phospholipid depots that are injectable through a fine needle. Advantageously, the gels are easily injectable through a fine needle even though they preferably have a high phospholipid content (e.g., 20-80%). The inventive gels are substantially uniform or one-phase, i.e., the pharmacologically active agent is uniformly distributed and remains uniformly distributed throughout the gel matrix, even after centrifugation at 1000 RPM for 5 minutes. This invention also relates to unique methods for the preparation of depots that allow for the intimate mixing or incorporation of water-soluble or solvent-incompatible drugs into phospholipid depots.

As such, in one embodiment, the present invention provides a one-phase gel composition, comprising:
20 to 80% by weight of one or more phospholipids;
optionally a pharmacologically active agent; and
0.1 to 70% by weight water, wherein the gel composition is extrudable through a 25 G ½ inch long needle from a 1 cc syringe at an extrusion rate of 2 cc/min by an applied force of no more than 12 pounds. The phospholipid depots are one-phase gels that can be aqueous or substantially anhydrous. In preferred embodiments, the formulation contains about 1 to about 20% pharmacologically active agent. In one embodiment, the optional pharmaceutical active ingredient is absent or not present and the gel is useful as a dermal filler.

In yet another embodiment, the present invention provides a method for preparing a one-phase gel composition, comprising:
a) forming a primary dispersion comprising one or more phospholipid(s) and an excessive amount of water;
b) homogenizing the primary dispersion to form a nanodispersion with an average particle size of about 30 nm to about 200 nm in diameter;
c) optionally passing the nanodispersion through a 0.2- or 0.45-micron filter; and
d) removing the excessive water to obtain a one-phase gel composition.

In certain embodiments, the one-phase gel is an aqueous gel. In other embodiments, the one-phase gel is substantially an anhydrous gel. In certain embodiments, the one-phase gel further comprises a pharmacologically active agent. When a pharmacologically active agent is present, it may be is added before step "b" or it may be added after step "b." In other embodiments, it may be added before as well as after step "b."

In other embodiments, the present invention provides a one-phase aqueous gel made by methods herein. The gel can be aqueous or a substantially anhydrous gel made by methods herein.

In certain embodiments, the aqueous or substantially anhydrous gels are transparent in appearance and silky smooth to the touch. Rheologically, the inventive gels are shear thinning and thixotropic, which are desired properties for good extrudability/injectability through a fine needle. In contrast, the same compositions, when prepared by known prior art methods, result in thick pastes that are very difficult or impossible to inject through a fine hypodermic needle.

These and other aspects, objects and embodiments will become more apparent when read with the accompanying detailed description and the figures that follow.

BRIEF DESCRIPTION OF THE DRAWINGS

FIG. 1A: aqueous gel (T-5) contains 37% water, but has no pharmacologically active agent in the T-5 composition as in EXAMPLE 1. FIG. 1B and FIG. 1C: aqueous gels each containing 100 unit/mL recombinant human insulin and 50% water but made with soy lecithin (FIG. 1B) or a synthetic phospholipid (POPC) (FIG. 1C), both as in EXAMPLE 3.

DETAILED DESCRIPTION OF THE INVENTION

I. Definitions

Figure 1:
FIG. 1 shows three translucent aqueous gels.

The phrase "Acceptable Injectability Criterion" as used herein includes quantitatively defining a formulation that requires an applied force of no more than 10 pounds to extrude the formulation from a 1 cc syringe through a 25 G ½ inch long needle at rate of 2 cc/min. In certain instances, the applied force is not more than 6 pounds, 7 pounds, 8 pounds, 9 pounds, 10 pounds, 10.5 pounds, 11 pounds, 12 pounds, 13 pounds, 14 pounds, 15 pounds, 16 pounds, 17 pounds, 18 pounds, 19 pounds or 20 pounds, to extrude the formulation from a 1 cc syringe through a 25 G ½ inch long needle at rate of 2 cc/min. Such a scenario represents typical conditions during the self-administration of insulin and other self-injected drugs.

The term "acidifying agent" includes a pharmaceutically acceptable acid such as hydrochloric acid, acetic acid, and sulfuric acid, and the like.

As used herein, the term "alkalizing agent" includes a pharmaceutically acceptable base such as sodium hydroxide, potassium hydroxide, ammonium hydroxide, lysine, arginine, and the like.

As used herein, the term "antimicrobial preservative" includes a pharmaceutical additive that can be added to an injectable pharmacologically active agent and be used to inhibit the growth of bacteria and fungi. The antimicrobial preservatives useful in this invention include, but are not limited to, cresols, phenol, benzyl alcohol, ethanol, chlorobutanol, parabens, imidura, benzylkonium chloride.

As used herein, the term "antioxidant" includes primarily reducing agents. The reducing agents useful in this invention include, but are not limited to, ascorbic acid or salts thereof, ascorbyl palmitate, sodium metabisulfite, propyl gallate, butylated hydroxyanisole, butylated hydroxytoluene, tocopherol, methionine or salts thereof, citric acid or salts thereof, reducing sugars, or mixtures thereof.

As used herein, the term "aqueous phase" includes a water solution containing pharmaceutically acceptable additives, such as acidifying, alkalizing, pH buffering, chelating, condensing and solubilizing agents, antioxidants and antimicrobial preservatives, tonicity/osmotic modifying agent, other biocompatible materials or therapeutic agents. In certain embodiments, such additives assist in stabilizing the pharmacologically active agent and depot compositions and in rendering the compositions biocompatible.

As used herein, the term "condensing agent" includes a pharmaceutically acceptable chemical that reduces solubility, alters release rate or increases stability of the pharmacologically active agent. For example, zinc ion forms insoluble crystals of with insulin and causes the insulin to release slowly. Other examples may include aluminum ions, ferric ions, protamine, or the like.

As used herein, the term "depot" includes a pharmacologically active agent delivery composition that is capable for releasing the pharmacologically active agent in a slow or controlled manner into the surrounding tissues to achieve a prolonged duration of action in comparison with the pharmacologically active agent without such composition. A depot composition may be administered by injection, instillation, or implantation into soft tissues, a certain body cavity or occasionally into a blood vessel with injection through fine needles being the preferred method of administration. A depot of pharmacologically active agent is intended to provide (1) convenient or less frequent dosing, (2) prolonged action, (3) improved safety and/or (4) better drug efficacy. The term "depot composition" can be used interchangeably with "sustained-release composition," "slow-release composition," "timed-release composition," "extended-release composition," "delayed-release composition," "long-acting composition," or "controlled-release composition."

As used herein, the term "emulsion" includes a mixture of immiscible oil phase and aqueous phase, where the oil phase comprises the oil and phospholipids and is in form of small droplets (the dispersed phase), which are suspended or dispersed in the aqueous phase (continuous phase). The primary emulsion formed in accordance with the present invention is typically optically opaque and possesses a finite stability.

As used herein, the term "a fine hypodermic needle" includes a small-diameter, hollow needle that is used with a syringe to inject substances into the body. The outer diameter of the needle is indicated by the needle gauge system. According to the Stubs Needle Gauge system, hypodermic needles in common medical use range from 7 gauge (the largest) to 33 (the smallest). The word "fine," as used herein, includes needles ranging from 21 to 33 gauge (G), preferably 25 G to 31 G and most preferably 25 G to 29 G. The definition for the fine hypodermic needle applies to both re-usable and disposable types. Disposable needles can be embedded in a plastic or aluminum hub that attaches to the syringe barrel by means of a press-fit or twist-on fitting or the "Luer Lock" connections or be permanently attached to the syringe barrel.

As used herein, the term "heat-sensitive pharmacologically active agent" includes a pharmacologically active agent that can lose 3% or more of its potency or concentration after autoclave treatment such as at 121° C. for 15-20 min. Some chemical drugs and many biological drugs are heat-sensitive. For these drugs, terminal sterilization procedures that use heat (or autoclaving) are not feasible.

As used herein, the term "injectable or extrudable" includes meeting the Acceptable Injectability Criterion as previously defined above.

As used herein, the term "insulin" includes a peptide hormone that is central to regulating carbohydrate and fat metabolism in the body, comprised of 51 amino acids and may be derived from various animal sources including bovine and porcine insulin or made by recombinant technology. The preferred insulin is a recombinant human insulin.

As used herein, the term "insulin analog" includes a chemically or enzymatically modified insulin wherein certain alteration is made to the peptide sequence or amino acid side chains in order to alter the pharmacodynamic or pharmacokinetic property of the insulin. The preferred insulin analogs include insulin lispro, insulin aspart, insulin glulisine, insulin glargine, and insulin detemir. The more preferred insulin analog is insulin glargine or insulin detemir.

In accordance with the practice of the present invention, lecithins used herein include pharmaceutical grade lecithins derived from egg or soybean, which have been used in parenteral products and are substantially free from irritating, allergenic, inflammatory agents or agents that cause other deleterious biological reactions. Other examples of phospholipids from naturally occurring sources that may be used for this invention include sphingolipids in the form of sphingosine and derivatives (obtained from soybean, egg, brain & milk), gangliosides, and phytosphingosine and derivatives (obtained from yeast).

As used herein, the term "metal ion chelating agent or chelator" includes a metal ion chelator that is safe to use in an injectable product. A metal ion chelator works by binding to metal ions and thereby reduces the catalytic effect of metal ion on the oxidation, hydrolysis or other degradation reactions. Metal chelators that are useful in this invention may include disodium edetate (EDTA), glycine and citric acid and the respective salts thereof.

As used herein, the term "nanodispersion" includes an emulsion or suspension formed by a homogenization step in the process for PG's. A nanodispersion of this invention contains phospholipid particles or oil droplets of a size less than 200 nm, preferably less than 100 nm and most preferably less than 50 nm. A nanodispersion may be referred to as a "nanoemulsion" if oil is present or "nanosuspension" if oil is not present in the composition.

As used herein, the term "nanodispersion" includes a suspension or emulsion with an average particle diameter of about 5 nm to about 200 nm, preferably about 5 nm to about 100 nm and more preferably about 5 nm to about 50 nm.

As used herein, the term "NPH insulin," or NPH includes Neutral Protamine Hagedorn (also known as HUMULIN® N, NOVOLIN® N, NOVOLIN® NPH, NPH Lletin II, and insulin isophane). NPH is a suspension of crystalline zinc insulin combined with the positively charged polypeptide, protamine and was created in 1936 when Nordisk formulated "isophane" insulin by adding Neutral Protamine to regular insulin. NPH insulin used herein also includes other insoluble insulin particles formed with zinc and/or protamine in ratios that are different from the insulin isophane.

As used herein, the term "oil" includes oil in a general sense to identify hydrocarbon derivatives, carbohydrate derivatives, or similar organic compounds that are liquid at body temperatures, e.g., about 37° C., and are pharmacologically acceptable in injectable formulations. "Oil" includes natural or synthetic glycerides or non-glycerides comprising synthetic triglycerides such as tricaprylin, triolein, or trimyristin, vegetable oil, animal oil, medium chain oil/glycerides, vitamin E, vitamin E acetate, vitamin E succinate, fatty acid, fatty acid monoester, cholesterol, and the like.

The term "one-phase" as used herein includes the ability of a PG to maintain a substantially uniform content for its key component, i.e., the pharmacologically active agent being uniformly distributed throughout the gel matrix, even after centrifugation at 1000 RPM for 5 minutes. In one aspect, a formulation that is one phase is "substantially uniform" wherein concentration of the pharmaceutically active agent in the different samples collected throughout a gel in a syringe or a bulk has a coefficient of variation (CV) less than about 1%, 2%, 3%, 4%, 5%, 6%, 7%, 8%, 9% or 10%.

The term "Phospholipid Gel" or "PG" as used herein includes a one-phase, transparent, translucent or opaque semi-solid mass (FIG. 1) that comprises 20-80% phospholipids and meets the "Acceptable Injectability Criterion."

As used herein, the term "pH buffering agent" includes a pharmaceutically acceptable pH buffer such as phosphate, acetate, citrate, bicarbonate, histidine, TRIS, and the like.

As used herein, the term "phospholipid" includes a lipid molecule containing one or more phosphate groups, including those derived from either glycerol (phosphoglycerides, glycerophospholipids) or sphingosine (sphingolipids). A phospholipid can be chemically synthesized or extracted from a natural source. Naturally occurring phospholipids are generally referred to as "lecithins." According to the United State Pharmacopoeia (USP), lecithin is a non-proprietary name describing a complex mixture of acetone-insoluble phospholipids, which are comprised mainly of phosphotidylcholine, phosphotidylethanolamine, phosphotidylserine and phosphotidylinositol, combined with various amounts of other substances such as triglycerides, fatty acids, and carbohydrates.

As used herein, the term "primary dispersion" includes an emulsion or suspension formed in the first step in a process of making the PG's of the present invention, that contain phospholipid particles or oil droplets of size greater than 500 nm in diameter. Such primary dispersions can be readily formed by simple mixing, such as stirring, or low speed agitation. A dispersion may be referred to as an "emulsion" if oil is present in the PG composition.

As used herein, the term "solubilizing agent" includes primarily cyclodextrins or surfactants such as polysorbate 80, bile salt and the like.

As used herein, a "sugar" includes a safe and biocompatible carbohydrate agent that protects the nanodispersion during drying by maintaining the discrete and sub-micron phospholipid particles. The sugars useful for this invention include, but are not limited to, monosaccharides, disaccharides, polysaccharides, propylene glycols, polyethylene glycols, glycerols, poly-ols, dextrins, cyclodextrins, starches, celluloses and cellulose derivatives, or mixtures thereof. For instance, in certain embodiments, the sugar is mannitol, sorbitol, xylitol, lactose, fructose, xylose, sucrose, trehalose, mannose, maltose, dextrose, dextran, or a mixture thereof. In certain embodiments, the preferred sugar is sucrose.

As used herein, the term "tonicity/osmotic modifying agent" includes a pharmaceutical additive that can be added to an injectable pharmacologically active agent and be used to adjust osmolality to close to 300 mOsm. The tonicity/osmotic modifying agents useful in this invention include, but are not limited to, potassium or sodium chloride, trehalose, sucrose, sorbitol, glycerol, mannitol, polyethylene glycol, propylene glycol, albumin, amino acid and mixtures thereof.

II. Embodiments

The present invention provides a one-phase gel composition, comprising:
  20 to 80% by weight of one or more phospholipids;
  optionally a pharmacologically active agent; and
  0.1 to 70% by weight water, wherein the gel composition is extrudable through a 25 G ½ inch long needle from a 1 cc syringe at an extrusion rate of 2 cc/min by an applied force of no more than 12 pounds. The phospholipid depots are one-phase gels that can be aqueous or substantially anhydrous. Preferably, the invention is directed to certain phospholipid compositions that are suitable for depot application.

Suitable synthetic phospholipids useful in the present invention include, but are not limited to:
  (1) Diacylglycerols, e.g. 1,2-Dilauroyl-sn-glycerol (DLG) and Dimyristoyl-sn-glycerol (DMG);
  (2) Phosphocholines, e.g. 1,2-Dimyristoyl-sn-glycero-3-phosphocholine (DMPC) and 1-Palmitoyl-2-Oleoyl-sn-glycero-3-phosphocholine (POPC);
  (3) Phosphoethanolamines, e.g. 1,2-Dimyristoyl-sn-glycero-3-phosphoethanolamine (DMPE) and 1,2-Palmitoyl-sn-glycero-3-phosphoethanolamine (POPE);
  (4) Phosphoglycerols, e.g., Egg phosphatidylglycerol, sodium salt (EPG, Na) and 1,2-Palmitoyl-sn-glycero-3-phospho glycerol, sodium salt (POPG, Na);
  (5) Phosphotidylserines, e.g. 1,2-Dimyristoyl-sn-glycero-3-phospho-L-serine, sodium salt (DMPS,Na) and 1,2-Dipalmitoyl-sn-glycero-3-phospho-L-serine, sodium salt (DPPS,Na);
  (6) Mixed Chain Phospholipids, e.g. 1-Palmitoyl-2-oleoyl-sn-glycero-3-phosphocholine (POPC) and 1-Palmitoyl-2-oleoyl-sn-glycero-3-phosphoglycerol, sodium salt (POPG,Na);

(7) Lysophospholipids, e.g. 1-Myristoyl-2-lyso-sn-glycero-3-phosphocholine (S-lyso-PC) and 1-Palmitoyl-2-lyso-sn-glycero-3-phosphocholine (P-lyso-PC); and (8) Pegylated Phospholipids, e.g. N—(Carbonyl-methoxypolyethyleneglycol 2000)-MPEG-2000-DPPE and 1,2-dipalmitoyl-sn-glycero-3-phosphoethanolamine, sodium salt.

The preferred synthetic phospholipids are POPC and DMPC.

In accordance with the practice of the present invention, the selection of a phospholipid for use in the depot compositions is determined by ability of the phospholipid to (1) form a nanodispersion and maintain the small particle size through the manufacturing process and afterwards in storage, (2) be chemically compatible with the pharmacologically active agent and (3) provide the desired depot or sustained release properties for the pharmacologically active agent. Certain combinations of phospholipids can be utilized to form the depot such as POPC and DMPC. An optional phospholipid or phospholipid combination for a depot composition can be selected using the physical and chemical screening test methods known to those skilled in the art.

In another embodiment, the PG compositions of the present invention comprise 20-80% by weight, 25 to 70% by weight, and more preferably 30 to 60% by weight of a phospholipid such as 25%, 30%, 35%, 40%, 45%, 50%, 55%, or 60% by weight of a phospholipid or a mixture of phospholipids.

In one embodiment, a PG that contains a significant amount of water, i.e., about 10% to about 70%, such as 10%, 15%, 20%, 25%, 30%, 35%, 40%, 45%, 50%, 55%, 60%, 65%, or 70%, and is referred to herein as "aqueous gel."

In another embodiment, a PG is essentially or substantially free of water, i.e., such as less than 5%, preferably less than 3% and more preferably less than 1%; such a PG is herein referred to as an "anhydrous gel." The water content can be a de minimus amount or about 0.01% to about 5%, or about 0.1% to about 5%, such as about 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, or about 5.0% w/w water.

In one embodiment, the present invention provides PG compositions containing pharmacologically active agents, satisfies the Acceptable Injectability Criterion and are able to deliver a pharmacologically active agent in a prolonged and peak-less PK profile.

In one embodiment, the present invention provides PG compositions compatible with heat-sensitive pharmacologically active agents of biological or synthetic chemical origin and methods of preparation of such PG compositions that permit sterilization by filtration of the nanodispersion intermediate through a 0.2- or 0.45-micron pore membrane, thus eliminating the need for an aseptic process or terminal sterilization using heat or radiation.

In another embodiment, the present invention provides aqueous gel PG compositions that are compatible with biological molecules such as insulin or other biologically active proteins or peptides, and methods to prepare such PG compositions, without the use of damaging amounts of organic solvent. Biological molecules are easily denatured or destroyed by organic solvents. However, in accordance with the teachings of the present invention, a solvent-incompatible biological molecule can be formulated into aqueous gels as a sustained-release depot.

In another embodiment, the present invention provides PG compositions that are essentially devoid of water (i.e., the anhydrous gels) in order to preserve water-sensitive pharmacologically active agents while retaining the acceptable injectability properties in the final product and the desired 0.2- or 0.45-micron sterile filtration step in the process.

In a preferred embodiment, the aqueous gels of the present invention comprises a biological molecule such as a protein, a peptide, a nucleic acid sequence, a virus, a cell line or a hydrophilic chemical drug or salt or solvate, and combinations thereof.

In another preferred embodiment, the PG gel of the present invention, either aqueous or anhydrous, comprises a heat-sensitive pharmacologically active agent such as a protein, a peptide, a nucleic acid sequence, a virus, a cell line or a sensitive chemical drug, which would be degraded or destroyed by heat or radiation typically used for terminal sterilization.

In yet another embodiment, the present invention provides an anhydrous gel that contains a water-sensitive pharmacologically active agent.

In yet another embodiment, the present invention provides anhydrous gels that contain lipophilic or water-insoluble pharmacologically active agents.

The present invention provides an anhydrous gel that can be used to dissolve highly water-soluble or hydrophilic pharmacologically active agents despite the fact that the gel is essentially water-free. For example, certain pharmacologically active agents in their salt forms, such as a sodium salt (e.g., sodium heparin) or a hydrochloride salt (e.g., lidocaine HCl), are extremely water-soluble and have very low solubility in oil or lipid. The invention methods to prepare anhydrous gel disclosed herein have allowed surprisingly high solubilization of such a highly hydrophilic pharmacologically active agents in anhydrous gels that essentially contain no water (EXAMPLES 5 and 6). The lidocaine HCl anhydrous gel is transparent and free of any insoluble solid particles. In contrast, using conventional methods to mix lidocaine with the other components of the anhydrous gel results in a suspension having most of the pharmacologically active agent remaining undissolved. This unexpected dissolution property, together with the absence of water of the anhydrous gel, provides an advantageous utility for forming depot compositions that contain pharmacologically active agents that are water-soluble yet sensitive to water, such as insulin and interferon.

The present invention provides aqueous gels that can be used to dissolve extremely water-insoluble or hydrophobic pharmacologically active agents despite the fact that the gels contain 20-70% water. For example, hydrophobic pharmacologically active agents such as docetaxel can be readily dissolved in an aqueous gel (EXAMPLE 7) and the resulting gel is transparent and free of any insoluble solid particles. This is in contrast to conventional methods, which would form a suspension with most of the hydrophobic pharmacologically active agent remaining undissolved following its addition into an aqueous composition. This unexpected dissolution property, together with the absence of solvent to promote the dissolution, provides an advantageous utility for forming depot compositions containing water-insoluble pharmacologically active agents without solvent or solvent-related safety concerns.

Table I below summarizes some, but not all, representative classes of the pharmacologically active agents that can be formulated as depots by the present invention.

TABLE I

| Water-soluble (Hydrophilic) | Stable in water | Heat-sensitive | Exemplary pharmacologically active agents | Applicable PG |
|---|---|---|---|---|
| | Classes of pharmacologically active agents | | | |
| Yes | Yes | Yes | Insulin (EXAMPLES 2-5, 19, 30, and 31) | Aqueous Gel & Anhydrous Gel |
| Yes | No | Yes | Buprenorphine HCl (EXAMPLE 6) | Anhydrous Gel |
| No | No | Yes | Docetaxel (EXAMPLE 7) | Anhydrous Gel |
| Yes | Yes | No | Lidocaine (EXAMPLE 8) | Anhydrous Gel |
| Yes | Yes | Yes | Exenatide (EXAMPLE 9) | Aqueous Gel |
| Yes | No | Yes | Beta Interferon (EXAMPLE 10) | Aqueous Gel |
| Yes | Yes | Yes | Heparin (EXAMPLE 11) | Aqueous Gel |
| Yes | Yes | Yes | Epotin Alpha (EXAMPLE 12) | Aqueous Gel |
| Yes | No | Yes | Human Growth Hormone (EXAMPLE 13) | Anhydrous Gel |
| Yes | No | Yes | Adalimumab(EXAMPLE 14) | Anhydrous Gel |
| Yes | No | Yes | Cefazolin & Metronidazole (EXAMPLE 15) | Anhydrous Gel |
| Yes | No | Yes | Bupivacane (EXAMPLE 16) | Anhydrous Gel |
| No | Yes | No | Predisone (EXAMPLE 20) | Anhydrous Gel |
| No | Yes | No | Ibuprofen (EXAMPLE 21) | Anhydrous Gel |
| No | Yes | No | Clotriamazole (EXAMPLE 22) | Anhydrous Gel |
| No | Yes | Yes | Risperidone (EXAMPLE 23) | Anhydrous Gel |
| No | No | No | Tamoxifen citrate (EXAMPLE 24) | Anhydrous Gel |
| No | Yes | No | Diazepan (EXAMPLE 25) | Anhydrous Gel |
| Yes | Yes | Yes | Insulin determir (EXAMPLE 30) | Aqueous Gel |
| No | No | Yes | NPH Insulin (EXAMPLE 31) | Aqueous Gel |
| Yes | Yes | Yes | BOTOX ® (EXAMPLE 32) | Aqueous Gel |

In a preferred embodiment, the phospholipid may be a lecithin, a synthetic phospholipid, or mixtures thereof. The preferred concentration of phospholipid is 20 to 80%, preferably 25 to 60%, and more preferably 30 to 50% such as 30%, 35%, 40%, 45%, or 50% of the PG weight.

In a preferred embodiment, oil may be used in the present invention's PG compositions. The oil may be synthetic triglycerides such as tricaprylin, trimyristin or triolein, vegetable oil, medium chain oil, vitamin E, vitamin E acetate, vitamin E succinate, oleic acid or other unsaturated fatty acids or their monoesters (e.g., ethyl oleate) or cholesterol, or mixtures thereof. The preferred oils are sesame oil, medium chain oil, ethyl oleate and the synthetic triglycerides and the preferred concentration of oil is 1 to 50%, preferably 2 to 20% and more preferably 5 to 10% of the PG weight, such as 5%, 6%, 7%, 8%, 9% or 10%.

In a preferred embodiment, a sugar can be used in the present PG compositions. The sugar may be sucrose, dextrose, lactose, glucose, trehalose, maltose, mannitol, sorbitol, glycerol, amylose, starch, amylopectin or mixtures thereof. The preferred sugars are sucrose and glycerol. The preferred concentration of sugar is 0.5 to 20%, preferably 1 to 15% and more preferably 2 to 10% such as 2%, 3%, 4%, 5%, 6%, 7%, 8%, 9% or 10% of the PG weight.

In a preferred embodiment, a solvent can be used in the invention PG compositions. The solvent may be ethanol, propylene glycol, glycerol, sorbitol, polyethylene glycol, silicone oil, glycofurol, ethyl oleate, or mixtures thereof. The preferred solvents are ethanol, glycerol and propylene glycol. The preferred concentration of solvent is 0.5 to 20%, preferably 1 to 15% and more preferably 2 to 10% such as 2%, 3%, 4%, 5%, 6%, 7%, 8%, 9% or 10% of the PG weight.

In one embodiment, the invention PG compositions may contain water. The preferred concentration of water is about 10 to 70% of the aqueous gel depot weight, and less than about 5%, preferably less than 3% or most preferably less than 1% of the anhydrous gel depot weight.

In one embodiment, the invention PG compositions may comprise a functional pharmaceutical excipient such as acidifying agents, alkalizing agents, pH buffering agents, metal ion chelators, antioxidants, stabilizers, preservatives, tonicity/osmotic pressure modifiers, condensing agents, or a mixture thereof. The selection of a functional excipient(s) in a PG composition can be made based on stability requirement or other pharmaceutical considerations known by those skilled in the art. Example excipients include, but are not limited to, HCl or NaOH for the pH adjuster, acetate or histidine for pH buffer, EDTA for the metal ion chelator, vitamin E, ascorbic acid or cysteine for the antioxidant, methionine for the stabilizer, meta-cresol, phenol or benzyl alcohol for the preservative, sodium chloride, glycerol or sucrose for the tonicity/osmotic pressure modifier, etc.

In one embodiment, the amount of active agent is about 0 to 20% by weight a pharmacologically active agent. In one embodiment, the invention PG composition does not contain any pharmacologically active agent or drug and such "drug-free" PG may be used as a tissue filler or as a wound salve.

In this embodiment, the optional pharmaceutical active ingredient is absent or not present.

In other embodiments, the PG contains about $1.0 \times 10^{-7}\%$ to about 1% by weight of a pharmacologically active agent. In other embodiments, the active agent is about 1 to about 20% such as 1, 2, 3, 4, 5, 6, 7, 8, 9, 10, 11, 12, 13, 14, 15, 16, 17, 18, 19, or 20% by weight of a pharmacologically active agent. In other embodiments, the amount is about 1% to about 6% or 3% to about 8% or even about 4% to about 11% by weight a pharmacologically active agent.

In one embodiment, the PG may contain about 0.1 nanogram/g up to 10 nanogram/g, such as 0.1, 0.2, 0.3, 0.4, 0.5, 0.6, 0.7, 0.8, 0.9, 1, 2, 3, 4, 5, 6, 7, 8, 9, or 10 ng/mL of an active ingredient such as BOTOX®, or about 0.6 to 4.8 nanogram/g or even about 0.6 to 4.8 nanogram/g of the formulation. In certain instances, the amount of active ingredient is around $1.0 \times 10^{-7}\%$ by weight. In certain instances, the active agent is present at about $1.0 \times 10^{-7}\%$ to about 1% by weight.

Certain embodiments are preferred. For example, in one embodiment, the present invention provides a one-phase aqueous gel composition comprising:
  20 to 80% by weight, preferably 25 to 70% by weight, and more preferably 30 to 60% by weight one or more phospholipid(s);
  10 to 70% by weight, preferably 20 to 60% by weight, and more preferably 40 to 60% by weight of water; and
  0 to 20% by weight a pharmacologically active agent, wherein the gel composition requires an applied force of no more than 15 pounds to be extruded from a 1 cc syringe through a 25 G ½ inch long needle at a rate of 2 cc/min.

In another embodiment, the present invention provides a one-phase anhydrous gel comprising:
  20 to 80% by weight, preferably 25 to 70% by weight, and more preferably 30 to 60% by weight one or more phospholipid(s);
  5 to 60% by weight, preferably 10 to 50% by weight, and more preferably 20 to 40% by weight a non-aqueous component selected from groups comprising sugar, oil, or solvent, and
  0 to 20% by weight a pharmacologically active agent, wherein the gel composition requires an applied force of no more than 15 pounds to be extruded from a 1 cc syringe through a 25 G ½ inch long needle at a rate of 2 cc/min.

Further, in accordance with the present invention, there are provided one-phase gel compositions comprising:
  (1) 20 to 80% by weight, preferably 25 to 50% by weight, and more preferably 30 to 40% by weight one or more phospholipid(s), and
  (2) 100 to 700 IU/g an insulin, insulin analog, a crystalline insulin with zinc and/or protamine, an NPH insulin or a combination thereof and water, wherein the gel composition requires an applied force of no more than 15 pounds to be extruded from a 1 cc syringe through a 25 G ½ inch long needle at a rate of 2 cc/min and maintains plasma glucose concentration below 130 mg/dl for no less than 18 hours following a subcutaneous injection of 20 IU/kg insulin dose into streptozotosin-induced type-I diabetic rats.

In a preferred embodiment, the PG compositions contain at least one pharmacologically active agent or drug. Suitable "pharmacologically active agents" contemplated for use herein are not limited by therapeutic category. Pharmacologically active agents can be small molecules made by synthetic chemistry or extraction ("chemical drugs") or biological drugs including proteins, peptides, oligonucleotides, viruses, cells, and the like. The PG compositions of the present invention have particular utility for heat-sensitive pharmacologically active agents, especially the biological drugs, such as insulin.

The preferred chemical drugs include, but are not limited to, antibiotics, anticancer agents, anesthetics, analgesics, hormones, antidiabetics and metabolic disorder drugs, with examples including cefazolin, metronidazole, bupivacaine, lidocaine, buprenorphine, paclitaxel, and docetaxel. The term chemical drugs also include salts, solvates isomers, active metabolites, or combinations of the chemical drugs.

The biological drugs contemplated for this invention include, but are not-limited to, biologically active agents selected from (a) blood proteins such as factor IXa, hemoglobin, protein C; (b) antibiotic peptide such as bactericidal/permeability-increasing protein (Bpi), magainin, peptidyl mimetics, protegrin, ramoplanin; (c) enzymes such as comasain, transforming growth factor, alpha-L-iduronidase, galactosidase, gelonin, glutamic acid, decarboxylase, ribonuclease, tpa variants; (d) antibodies such as anti-EFGr, anti-lymphoma antibody, anti-Her2, anti-Cd11/Cd18 integrin, anti-integrin receptors, anti-Cd52; (e) hormones such as amylin, extendin-4, relaxin, bone growth factors, epidermal growth factor, fibroblast growth factor, hematopoietin, insulin, insulin-like growth factor-1, leptin, natriuretic peptides, neural growth factors, parathyroid hormone, thrombopoietin, thymosin alpha-1: (f) enzyme inhibitors such as angiostatin and endostatin, bivalirudin, nematode anticoagulant proteins; (g) vaccines; (h) lymphokines such as interleukin-4, interleukin-6, interleukin-10, interleukin-12, (h) stem cell factor; (i) myeloid progenitor inhibitory factor-1, macrophage colony-stimulating factor, botulinin, fusion proteins, collagen, surfactant protein, protamine sulfate and heparin. The term biological drugs also include salts, solvates isomers, active metabolites, or combinations of the biological drugs.

The preferred biological drugs include, but are not limited to, insulin, interferon, growth hormone, calcitonin, parathiroid hormone, exernatide, pramlintide, heparin, granulocyte colony-stimulating factor (G-CSF), epoetin, adalimumab, trastuzumab, and mixtures thereof.

In one embodiment, the present invention provides PG compositions, which contain insulin and satisfies the Acceptable Injectability Criterion and are able to maintain a plasma glucose concentration below 130 mg/dl for no less than 18 hours following a subcutaneous injection of a 20 IU/kg insulin dose into streptozotosin-induced type-I diabetic rats.

In another embodiment, the insulin contained in the PG compositions of the present invention is of animal origin or is a recombinant insulin, a human recombinant insulin, a insulin complex with zinc, protamine or a combination thereof, an insulin analog or a mixture thereof.

In yet another embodiment, the PG composition of the present invention that contains insulin comprises 50 to 1000 IU/g, preferably 100 to 500 IU/g, more preferably 100 to 400 IU/g such as 100 IU/g, 200 IU/g, 300 IU/g, 350 IU/g or 400 IU/g or most preferably 100 IU/g insulin, insulin analog or NPH insulin. In certain aspects, 100 IU is about 3.8 mg of recombinant human insulin. In still another embodiment, the PG composition of the present invention that contains insulin comprises about 0.1% to about 5%, preferably about 0.3% to about 5% such as 0.3, 0.4, 0.5, 0.6, 0.7, 0.8, 0.9, 1.0, 2.0, 3.0, 4.0 or 5.0% insulin.

In certain embodiments, the one-phase gel composition of the present invention maintains a peak-less blood insulin vs time profile in streptozotosin-induced type-I diabetic rats within 24 hours following a subcutaneous injection of 20 IU/kg insulin, and wherein the insulin concentration ratio of the highest point to the lowest is no more than 6:1, no more than 5:1, no more than 4:1, or even no more than 3:1.

In one embodiment, the present invention provides certain PG compositions that contain 20 to 80% by weight of one or more phospholipids and surprisingly satisfies or requires even less injection force than the Acceptable Injectability Criterion. In some other embodiments, the present invention provides certain PG that requires greater injection force than the Acceptable Injectability Criterion and such PG's may be delivered through a large needle into certain body cavity such as a surgical wound.

In another preferred embodiment, this invention relates to PG compositions, in their injectable, stable and sterilized form, that provide a unique drug release profile that is prolonged and peak-less. Such release profile is highly desirable for certain drugs with short half-lives, such as insulin, and permit them to be maintained at constant levels in the circulation for a prolonged time. In a preferred embodiment, the PG compositions and achieve a 24 hr duration PD and peak-less 24 hr duration PK profiles for human insulin.

In another preferred embodiment, the PG composition of the present invention has at least one of the properties listed below, and is suitable as a replacement for NPH basal insulin therapy:
1. Incorporates authentic human insulin (as in NPH);
2. Administered by the same route as NPH, i.e., subcutaneous injection;
3. Delivers a 24 hr peak-less PK profile;
4. Provides a 24 hr PD profile that is significantly longer than that shown for NPH;
5. Has a stability/shelf-life comparable to the NPH drug;
6. Is injectable through a fine needle, i.e., 25 G or smaller;
7. Has significantly improved dose-uniformity (i.e., injection-to-injection variability of <3% relative standard deviation);
8. Is ready to use and does not require mixing prior to injection;
9. Is injectable by pen injector;

In another embodiment, the PG compositions and methods of preparation disclosed herein are useful for both synthetic and biological drugs. The PG compositions are especially useful for biological drugs having physical and chemical properties similar to insulin, i.e., highly water soluble, solvent-incompatible, and sensitive to heat or radiation.

The present invention provides PG compositions and their methods of preparation which have the following unexpected features:
(1) High phospholipid content (i.e., 20-80%).
(2) Surprisingly good injectability.
(3) Filterable through 0.2-0.4 micron filters to enable a sterilization-by-filtration in the manufacturing process, thus permitting PGs to be used with heat- and radiation sensitive drugs.
(4) Compatible with water-soluble or solvent-incompatible synthetic and biological pharmacologic agents.
(5) Prolonged and peak-less delivery profile-capable for certain drugs such as insulin.

III. Methods of Making

Figure 4:
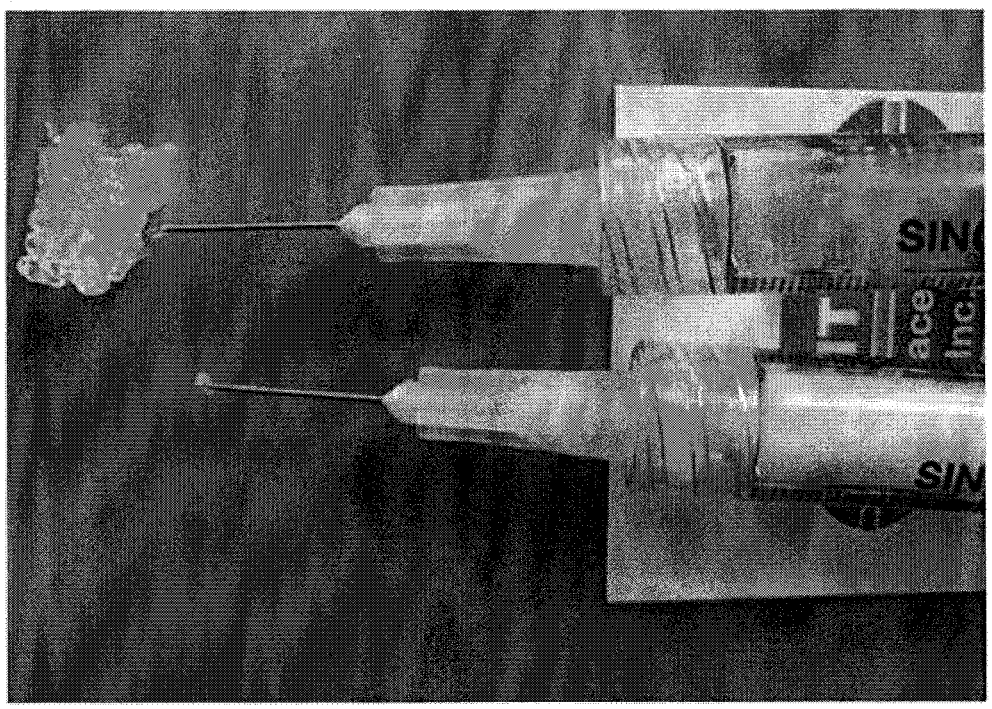
FIG. 4 shows difference in injectability through 27 G needles after 5-second manual extrusion using 1 mL syringes between two phospholipid preparations containing the same composition (T-4) as in EXAMPLE 1 but prepared by different methods. The clear gel is an anhydrous gel (in top syringe) and was prepared according to the method in EXAMPLE 1 and the opaque gel (bottom syringe) was prepared by the method taught in other prior arts wherein all components were mixed and homogenized. After applying the same force and duration to the syringes, substantially more aqueous gel was ejected, compared to the opaque paste prepared according to other existing methods.

Surprisingly, the aqueous gels and anhydrous gels that are prepared according to the methods of preparation of the present invention are easily injectable through fine needles even with their high phospholipid content (e.g., 20-80%). In some formats, the aqueous gels or anhydrous gels are transparent in appearance and silky smooth to the touch. Rheologically, these gels are shear thinning and thixotropic, which are desired properties for good extrudability/injectability through a fine needle. In contrast, the same compositions, when prepared by other known prior art methods, result in thick pastes that are very difficult or impossible to inject through a fine hypodermic needle (FIG. 4).

In one embodiment, the present invention provides a method for preparing a one-phase gel composition, the method comprising:
a) forming a primary dispersion comprising one or more phospholipid(s) and an excessive amount of water;
b) homogenizing the primary dispersion to form a nanodispersion with an average particle size of about 30 nm to about 200 nm in diameter;
c) optionally passing the nanodispersion through a 0.2- or 0.45-micron filter; and
d) removing the excessive water to obtain a one-phase gel composition.

In certain embodiments, the one-phase gel is an aqueous gel. In other embodiments, the one-phase gel is substantially an anhydrous gel. In certain preferred embodiments the one-phase gel further comprises a pharmacologically active agent. When a pharmacologically active agent is present, it may be is added before step "b" or it may be added after step "b". In other embodiments, it may be added before as well as after step b. In other embodiments, the present invention provides a one-phase aqueous gel (e.g., aqueous or a substantially anhydrous) made by methods herein.

In addition, with regard to step "c" of passing the nanodispersion through a 0.2- or 0.45-micron filter, if included, the filtration step can be performed either before or after "removing the excessive water" step in making an aqueous or an anhydrous gel. Thus, in certain aspects, step "c" is included in the method, or in certain aspects, step "c" is performed after step "d". In certain aspects, the filtration step can be eliminated and the PG is sterilized by heat or radiation or prepared aseptically.

In another embodiment, the present invention relates to unique methods to prepare sterile PG compositions that are filterable through a 0.2- to 0.45-micron pore membrane to permit sterilization of the PG preparation by filtration, yet have a 20 to 80% by weight phospholipid content and are able to meet or require less force than the Acceptable Injectability Criterion.

In another embodiment, the present invention provides unique methods to prepare PG compositions to contain water-soluble or solvent-incompatible drugs such as insulin without any precipitation or degradation of the insulin, yet having about 20 to 80% by weight phospholipid content and require less injection force than the Acceptable Injectability Criterion.

Figure 5:
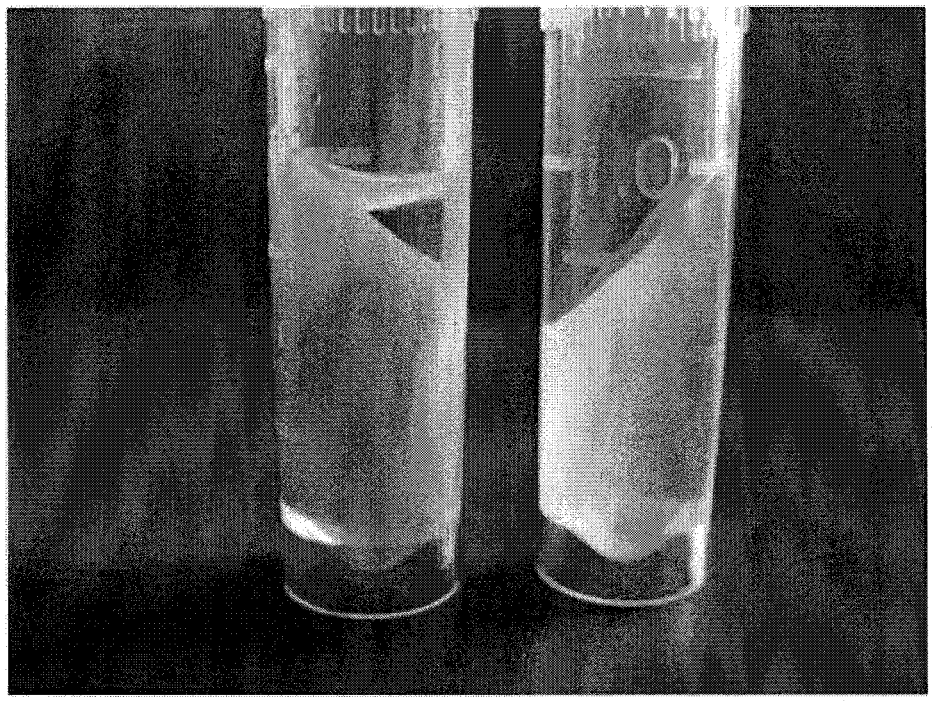
FIG. 5 illustrates the superior uniformity and physical stability of an aqueous gel produced using the methods of the present invention (right, T-4 as in EXAMPLE 1) compared to a paste produced by mixing the same components but using a different process than the aqueous gel (left). After centrifugation (13,000 rpm, 10 minutes), the paste separates into liquid and solid phases whereas the aqueous gel remains as a uniform, single-phase gel.

More surprisingly, the aqueous gels prepared according to the present invention exhibit superior uniformity and physical stability over a composition containing the same components, but prepared by methods taught in prior art. FIG. 5 illustrates the superior uniformity and physical stability of an aqueous gel produced according to EXAMPLE 1 (right, T-4) over a paste resulting from mixing the same components but not using the methods of the present invention to prepare the aqueous gel (left). After centrifugation (13,000 rpm, 10 minutes), the paste produced by a prior art method separates into liquid and solid phases whereas the aqueous gel prepared in accordance with the present invention remains as a uniform, single-phase gel (Example 27). Such content uniformity is key for accurate dosing as well as the physical stability required for adequate product shelf life for pharmaceutical products.

In a preferred embodiment, a high-shear, high-energy or high-pressure homogenizer (such as the microfluidizers from Microfluidics International Corporation) is used to convert the primary dispersion to a nanodispersion by reducing the phospholipid particles in the primary dispersion from more than 500 nm to less than 200 nm, preferable less than 100 nm and most preferably less than 50 nm. The reduction of phospholipid particles greatly reduces viscosity and increases the injectability of the final PG's. For example, before high-pressure homogenization, a primary dispersion composition containing about 20% phospholipid is a white, opaque, thick yogurt-like mass and is not injectable through a 25 G needle.

After homogenization in a microfluidizer to reduce the lipid diameter to about 50 nm, the resulting nanodispersion is a clear, transparent, thin and water-like liquid with a remarkably reduced viscosity. After removing the excessive water, the final PG satisfies the Acceptable Injectability Criterion. The nanodispersion can also be filtered through a 0.2- or 0.45-micron filter membrane, allowing sterilization of the PG preparations prior to parenteral administration. In contrast, the same phospholipid-containing composition without the homogenization treatment is not filterable through the same membranes.

In a preferred aspect, the present invention provides a method for preparing a one-phase aqueous gel composition, comprising:
  a) mixing the components to form a primary dispersion comprising one or more phospholipid(s) and excessive water;
  b) homogenizing the primary dispersion to form a nanodispersion with an average particle size of less than about 200 nm in diameter;
  c) passing the nanodispersion through a 0.2- or 0.45-micron filter; and
  d) removing the excessive water to obtain the aqueous gel.

In another embodiment, the present invention provides a method for preparing a one-phase anhydrous gel comprising:
  a) mixing the components to form a primary dispersion comprising one or more phospholipid(s), and excessive water;
  b) homogenizing the primary dispersion to form a nanodispersion with an average particle size of less than about 200 nm in diameter;
  c) passing the nanodispersion through a 0.2- or 0.45-micron filter; and
  d) removing water to less than 5%, preferably less than 3% and more preferably less than 1% by wt of the anhydrous gel.

Additionally, in accordance with the present invention, there are provided one-phase anhydrous gel compositions comprising:
  a) mixing the components to form a dispersion comprising one or more phospholipid(s), excessive water;
  b) removing water to less than 5%, preferably less than 3% and more preferably less than 1% by wt of the anhydrous gel;
  c) adding a solvent;
  d) mixing to obtain an anhydrous gel, and
  e) passing the gel though a 0.2- or 0.45-micron filter.

In one particular aspect of making an anhydrous gel, it is not required to homogenize the primary dispersion. This is especially advantageous with a PG formulation without an active ingredient or with a non-heat sensitive or radiation sensitive active ingredient.

According to the present invention, a primary dispersion contains at least about 70-80% water, which is more than needed in the final PG's. However, this amount of water gives the dispersion the desired flow properties in order to be processed in the microfluidizer. Once the nanodispersion is obtained, the excessive water is removed in order to achieve the final water content in the PG of 20 to 70% for an aqueous gel or less than about 5%, preferably about 3%, or more preferably about 1% water content for an anhydrous gel so that the PG will have the desired properties. In accordance with the practice of the present invention, it is important to maintain the small phospholipid particle size during the water-removing (drying) step to maintain the low viscosity or high injectability of the final PGs.

Emulsions or suspensions of phospholipids are thermodynamically unstable systems. If not processed properly, the phospholipid droplets or particles will aggregate, merge, grow in size and eventually result in the phospholipid and separating the water phases (i.e., creaming out). When this happens the benefit of the reduced viscosity provided by the nanodispersion is lost. Surprisingly, in accordance with the practice of the present invention, the addition of certain sugars provides an unexpected protective effect for the nanodispersion against the aggregation of phospholipid particles or droplets during the water removal processes. The presence of sugar in the nanodispersion thus keeps the phospholipid nanodispersion particle size essentially unchanged during the water removal step using the conditions disclosed herein.

In certain aspects, as shown in Examples 1 and 2, the resulting aqueous gels have about the same particle size as in the nanodispersion, while maintaining excellent injectability properties for injections through fine hypodermic needles (FIG. 4). The present inventors have observed that as water is removed from the nanodispersion to where the PG reaches a water content of 50% or less, a phase transition occurs that turns the solution-like nanodispersion into a gel. The PG thus foamed is transparent or translucent, one-phase and remains one-phase even after being subjected to a strong separation force such as centrifugation. Upon mixing in water, the PGs of this invention can re-form the nanodispersion, suggesting that the PGs comprise discrete nanometer-sized phospholipid particles.

In contrast, following other known prior art methods that simply mix the same PG components, even with vigorous agitation for 24 hours, the same compositions as in Example 1 and 2 produced a pasty mass, which is opaque, not one-phase and did not satisfy the Acceptable Injectability Criterion (FIG. 4).

Figure 9:
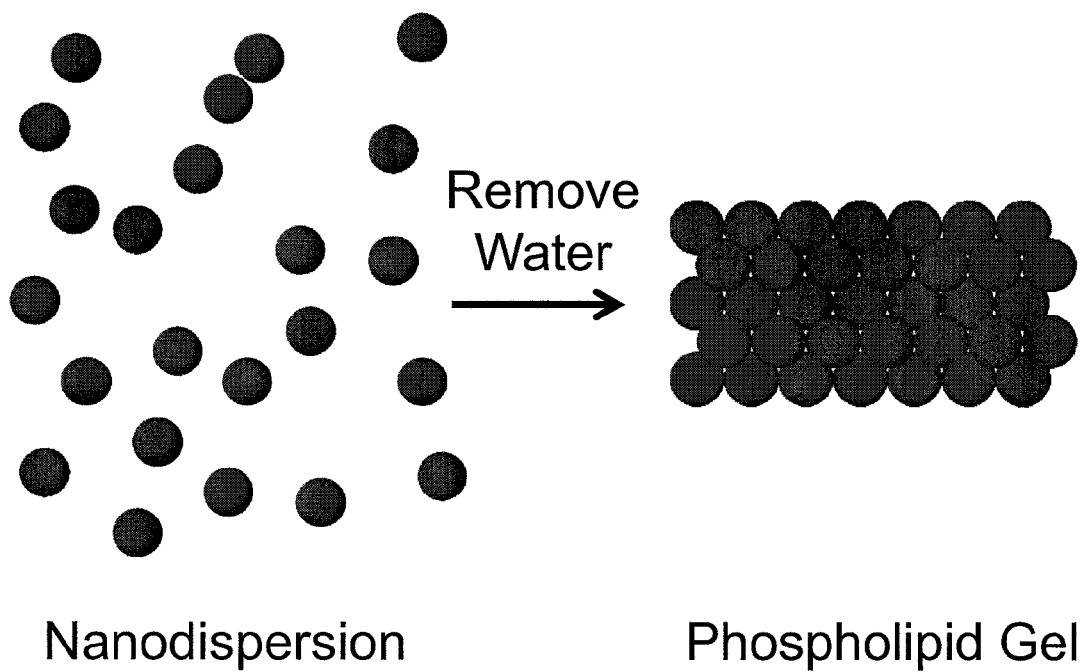
FIG. 9 is a schematic representation of the speculated conversion from a nanodispersion (left) to a PG (right) upon removal of water. The circles depict the nanosized phospholipid particles in the nanodispersion, and the space between the dots are filled with water as in an aqueous gel or oil as in an anhydrous gel.

Not wishing to be bound by a theory or mechanism of the invention, it appears that the superior injectability offered by the PG's of this invention is attributable to the extremely small phospholipid particles created by homogenization. This inventor speculates that by removing the water from the nanodispersion, the nanometer sized phospholipid particles stack together to form a certain organized structure like many small deformable "balloons" filled with oil and stacked together with water in the interstitial space. As the water is removed, the interstitial space is minimized causing the balloons to deform to compress into each other to form a more rigid structure i.e., a gel, but rather than fusing into each other, the balloons remain discrete in the gel phase. When an external force is applied (such as from a syringe plunger), the gel easily deforms and conforms to the needle bore because of the very small and discrete phospholipid particles, thus allowing for a superior injectability. FIG. 9 is a schematic representation of the speculated convention from a nanodispersion (left) to a PG (right) upon removal of water. The dark dots depict the nanosized phospholipid particles in the nanodispersion, and the space between the dots are filled with water as in an aqueous gel or sugar or oil as in an anhydrous gel. As the water or solvent is removed, the particles become structurally organized into the gel.

Depending upon stability of the pharmacologically active agent and drug delivery/release requirements, a pharmacologically active agent can be introduced at a different step during the present invention's process according to the present methods.

In one embodiment, the present invention provides a method for dissolving the pharmacologically active agent in the aqueous phase that can then be mixed with the phospholipid to form the primary dispersion that is subsequently carried through the rest of the process. The methods may be used for a water-soluble pharmacologically active agent and when the pharmacologically active agent is shear stress-resistant and/or a slower drug release is desired.

In another embodiment, the present invention provides methods to dissolve the pharmacologically active agent in an oil phase, which contains the phospholipids and, optionally oil, which can then be mixed with the aqueous phase to form the primary dispersion that is subsequently carried through the rest of the process. This method may be used for a lipophilic, water-insoluble or fat-soluble pharmacologically active agent.

In yet another embodiment, the present invention provides a method for introducing the pharmacologically active agent into the primary dispersion prior to the homogenization step which is subsequently carried through the rest of the process.

In another embodiment, the present invention provides a method for introducing the pharmacologically active agent into the nanodispersion after the homogenization step which is subsequently carried through the rest of the process.

In yet another embodiment, the present invention provides a method for introducing the pharmacologically active agent into the gel after the water removal step.

In one embodiment, the primary dispersion is made by mixing the oil phase containing phospholipid and other fat-soluble components with an aqueous phase which contains all water-soluble components. Alternatively, the primary dispersion is made by mixing all components with no particular order of addition.

In another embodiment, the oil phase is made by mixing the phospholipid and, optionally oil and the pharmacologically active agent. Alternatively, the oil phase is made by dissolving the phospholipid, the pharmacologically active agent and, optionally oil in a volatile solvent such as ethanol and then removing the ethanol.

In one embodiment, the aqueous phase is made by mixing water, pH adjuster, pH buffer, chelator, antioxidant, stabilizer, preservative, and/or tonicity/osmotic pressure modifier to form a solution. Optionally, a pharmacologically active agent may be dissolved or added to the aqueous phase.

In another embodiment, the filtration of the nanodispersion may be performed using a vacuum filtration method, centrifugation filtration, or pressurized filtration method. Various models or makes of 0.2- or 0.45-micron pore filter membranes are available.

Examples include Sartopore, Sartobran P, Millipore, and the like. In some cases, a pre-filter with a larger pore size may be used. The primary reason for the filtration step is to sterilize the preparation.

In yet another embodiment, removal of water from the dispersion or nanodispersion can be done by various drying methods, for example, by rotational vacuum drying method or by sweeping the nanodispersion with air or nitrogen gas ("air drying"). The rotational vacuum drying can be performed using commercially-available rotational evaporators such as a Rotavap (Buchi). The air drying is accomplished by mechanically stirring the nanodispersion while sweeping its surface with a stream of air or nitrogen gas. The air or nitrogen gas may be filtered through a 0.2- or 0.45-micron pore filter to sterilize. Nitrogen gas is preferred if any components in the composition are prone to oxidation.

In one embodiment, a solvent is added to form the anhydrous gel, to 0.5 to 20%, preferably 1 to 15% and more preferably 2 to 10% of the anhydrous gel weight to improve the injectability/filterability. An example of the suitable solvents is ethanol, which could be added from 1 to 10% by weight. Prior to adding to the gel, the solvent may be first sterilized (e.g., by filtration through a 0.2- or 0.45-micron rated filter). After addition, the mixture is agitated to form a uniform anhydrous gel.

In another embodiment, the anhydrous gel containing the solvent is sterilized by filtration through a 0.2- or 0.45-micron pore filter at the end of the process.

In some embodiments, the aqueous or anhydrous gels are filled into syringes to certain volume under aseptic conditions and are ready for injecting after attaching needles to the syringes. The pre-filled syringe format is convenient for self-administration. The preferred syringe size is 1-10 mL and the preferred needle size is 25-29 G.

Figure 2:
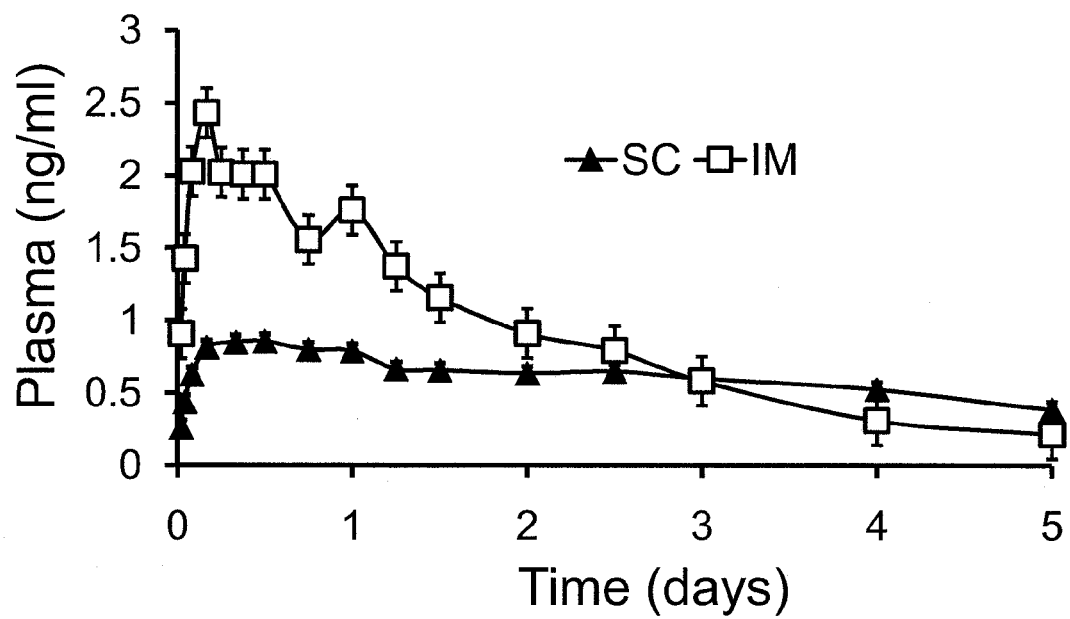
FIG. 2 illustrates pharmacokinetic profile in dogs following a subcutaneous (SC) or intramuscular injection (IM) at 0.25 mg/kg dose of buprenorphine in an anhydrous gel (F-27 as in EXAMPLE 6).
Figure 7:
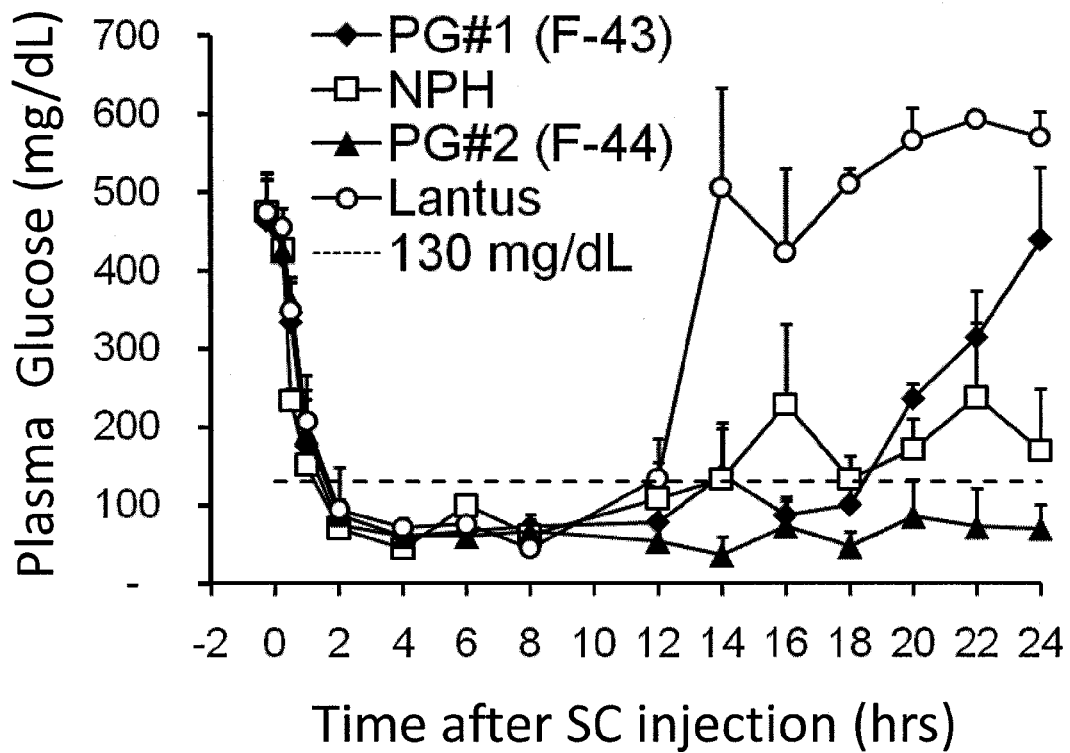
FIG. 7 shows blood glucose levels following a subcutaneous injection of a 20 IU/kg insulin dose for four different basal insulin formulations in the streptozotosin (STZ)-induced type-I diabetic Sprague Dawley rat animal model. Data points are mean values from 3 rats and error bars represent the standard error of the mean.
Figure 8:
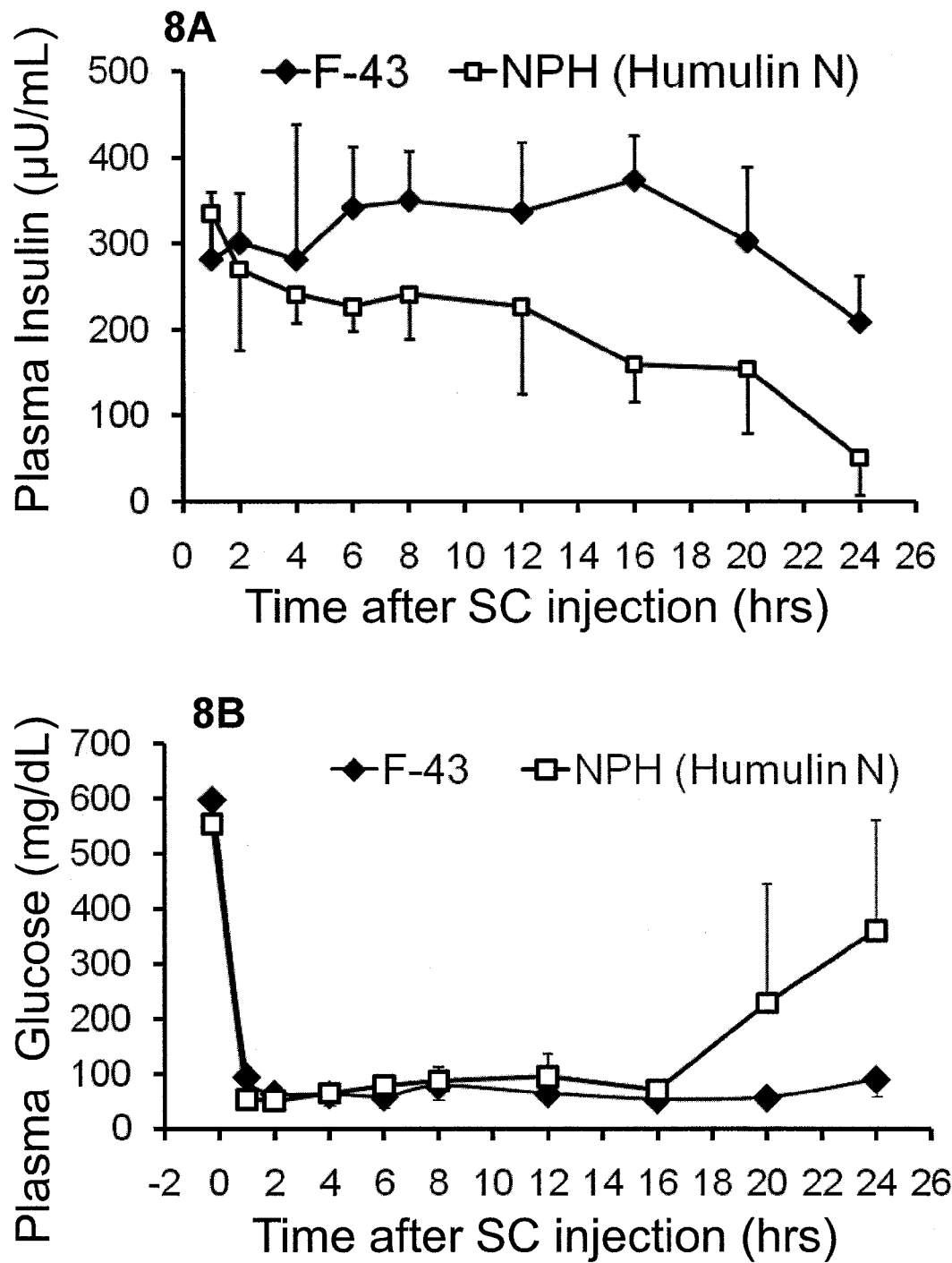
FIG. 8 shows the plasma insulin levels (upper panel) measured using a human insulin ELISA kit and the blood glucose levels (lower panel) measured by a glucometer following subcutaneous injection of two different basal insulin formulations in the streptozotosin (STZ)-induced type-I diabetic Sprague Dawley rats. Data points are mean values from 4 rats and error bars represent the standard error of the mean.

In one embodiment, the aqueous or anhydrous gels, after being injected into a soft tissue (e.g., subcutaneous or intramuscular injection), provide a slow drug release in vivo as shown by a prolonged plasma drug concentration-time profile, compared to the same pharmacologically active agent without a depot composition. The preferred profile covers 1, 3, 5, 7, 10 and 14 days (FIG. 2, FIG. 7 & FIG. 8).

Figure 3:
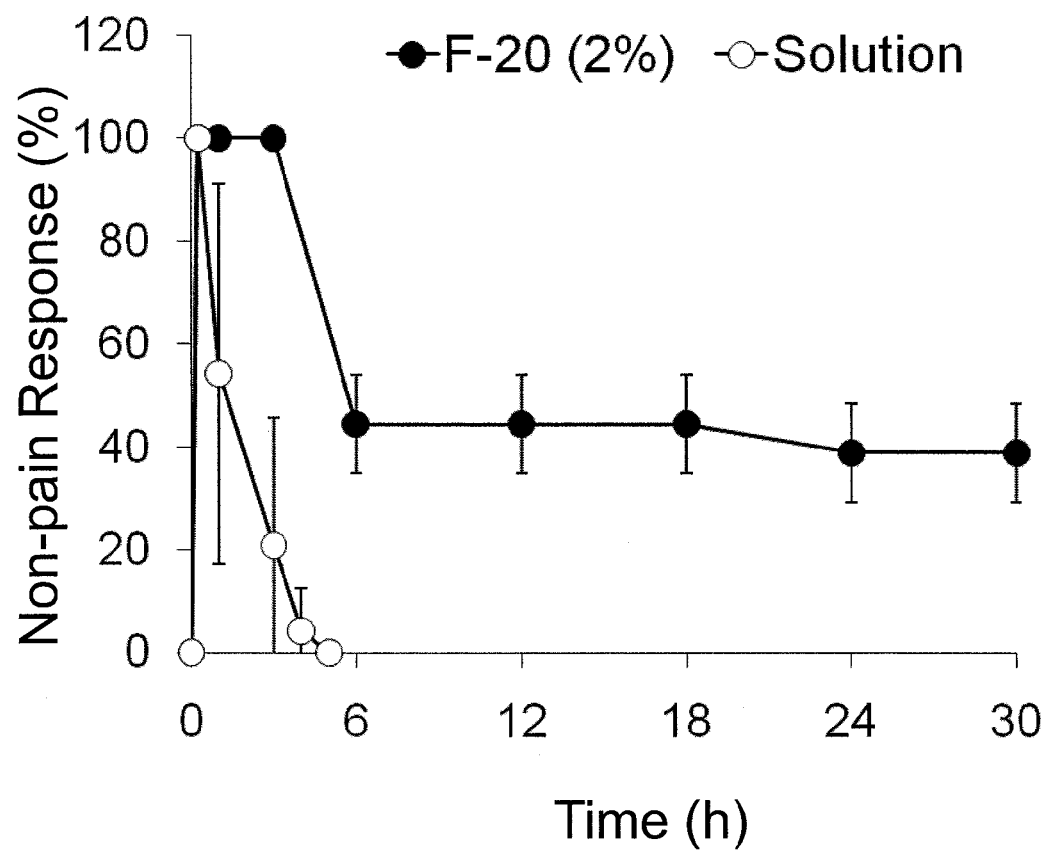
FIG. 3 illustrates prolonged local analgesic/anesthetic efficacy of lidocaine in an anhydrous gel (F-20 as in EXAMPLE 8) in guinea pigs following an intracutaneous injection compared to placebo anhydrous gel.

In another embodiment, the aqueous or anhydrous gels, after being injected into a soft tissue (e.g., subcutaneous or intramuscular injection), provide a prolonged drug residence time at the injection site as shown by a maintained drug concentration or a sustained local drug activity at the injection site-time profile compared to the same drug without a depot composition. The preferred profile covers 1, 3, 5, 7, 10 and 14 days (FIG. 3, FIG. 7 & FIG. 8).

In certain aspects, the formulation has a dynamic viscosity of about 100, 200, 500, 1000, 3000, and 5000 centipoise (cP). In certain aspects, the dynamic viscosity of the formulation is at about 5000, 10,000, 50,000, 75,000, $1\times10^5$, $1\times10^6$, $1\times10^7$, $1\times10^8$ or $1\times10^9$ cP at STP. In yet other aspects, the formulation is thixotropic.

In certain aspects, the PG formulation of the present invention is acidic to neutral. In certain aspects, the formulation has a pH of about 3 about 8.5. In certain other aspects, the formulation has a pH from about 5 to about 8.5, from about 5.5 to about 8.1, about 6 to about 7.9, about 5.5 to about 7.9, or from about 6.5 to about 7.5.

In a preferred aspect, the PG formulations of the present invention comprise a pH-adjusting agent. In one embodiment, the pH-adjusting agent is a base. Suitable pH-adjusting bases include amines (e.g., diethanolamine or triethanolamine), bicarbonates, carbonates, and hydroxides such as alkali or alkaline earth metal hydroxides as well as transition metal hydroxides. The pH-adjusting agent is preferably sodium hydroxide and is present in an amount sufficient to adjust the pH of the composition to between about pH 4.0 to about 8.5; more preferably, to between about pH 5.5 to about 7.0, such as 6.0 or 6.5. Alternatively, the pH-adjusting agent can also be an acid, an acid salt, or mixtures thereof. In a preferred embodiment, the pH-adjusting agent is an acid.

Further, the pH-adjusting agent can also be a buffer. Suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, ammonium/ammonia buffers, and the like. In certain embodiments, the buffer is an acidic buffer system (e.g., benzocaine).

The invention will now be described in greater detail by reference to the following non-limiting examples.

Example 1

Preparation of Aqueous Gels (Having No Pharmaceutically Active Agent) Using Lecithin

| | Compositions | | | |
|---|---|---|---|---|
| | F-1 | | | |
| | (Wt % in primary | T-3 | T-4 | T-5 |
| Component | dispersion) | (Wt % in PG) | | |
| Sesame oil | 4.0 | 6.6 | 8.0 | 10.1 |
| Soy lecithin | 15.0 | 24.7 | 30.2 | 38.0 |
| Cholesterol | 0.6 | 1.0 | 1.2 | 1.5 |
| Vitamin E succinate (VES) | 0.3 | 0.5 | 0.6 | 0.8 |
| Sucrose | 5.0 | 8.2 | 10.1 | 12.7 |
| De-ionized water (DI-water) | 75.1 | 59.0 | 50.0 | 37.0 |
| Total | 100 | 100.0 | 100.0 | 100.0 |

| | Components | |
|---|---|---|
| Name | Supplier | Grade |
| Sesame oil | Croda | Super-refined, USP |
| Soy lecithin (Phospholipon 90G) | LIPOID | EP |
| Cholesterol | Solvay Pharmaceuticals | HP, NF |
| VES | Spectrum Chem. | USP |
| Sucrose | Spectrum Chem. | NF |
| De-ionized water | Latitude Pharmaceuticals Inc. | |

Procedure

The F-1 primary dispersion first was prepared and converted to three aqueous gels (T-3, T-4 and T-5) by the following procedure:
  1. Weigh out sesame oil, Phospholipon 90G and cholesterol into a glass flask.
  2. Add 50 mL ethanol USP.
  3. Rotate the flask to dissolve all solids.
  4. Vacuum dry to remove ethanol to less than 1% by weight.
  5. Add VES (in a 5% stock solution), sucrose and DI-water to 500 g total weight.
  6. Rotate the flask to mix to form a primary dispersion.
  7. Homogenize the primary dispersion using a Microfluidics International Corp Model M-110EH to obtain a nanodispersion. Continue the process until the average particle diameter is about 69 nm as determined by laser light scattering (Malvern Nano Zetasizer). Record pH which is 5.9
  8. Filter the nanodispersion through a 0.45-micron disposable vacuum filter (Nalgene) in a biosafety hood to sterilize.
  9. Aseptically, remove water by a rotational evaporator (Buchi Model R-205 Rotavap) until the water content is about 59%, 50% and 37% by weight to obtain respectively, T3, F-4 and T-5.

The T-3, T-4 and T5 were one-phase, uniform, and translucent/transparent gels (FIG. 1) that were readily injectable and met the Acceptable Injectability Criterion defined herein. Their water contents were confirmed by a moisture balance. The average particle sizes after being re-dispersed in water were determined as 63, 62 and 56 nm, respectively, for T-3, T-4 and T-5, as determined by laser light scattering. All three gels were filterable through 0.2-micron filters.

The compositions of this example can be used as tissue fillers for various indications such as cosmetic wrinkle removal.

Example 2

Preparation of Aqueous Gels Containing Recombinant Human Insulin for Basal Insulin Therapy Aqueous gels containing recombinant human insulin and 40%, 50% and 60% water were prepared using lecithin. Insulin was introduced into the process before microfluidization and the resulting nanodispersion was filtered for sterilization. Thus, no heat or radiation sterilization was needed in the process.

| | Compositions (% wt) | | | |
|---|---|---|---|---|
| | Nanodispersion | Aqueous Gel | | |
| Component | F-1 | F-2 | F-3 | F-4 |
| Recombinant human insulin | 74.9 (IU/g) | 84.9 (IU/g) | 100 (IU/g) | 115.4 (IU/g) |
| Sesame oil | 4.0 | 6.43 | 8.03 | 9.64 |
| Soy lecithin | 15.0 | 24.10 | 30.12 | 36.14 |
| Cholesterol | 0.6 | 0.96 | 1.20 | 1.45 |
| Vitamin E succinate (VES) | 0.3 | 0.48 | 0.60 | 0.72 |
| Sucrose | 5.0 | 8.03 | 10.04 | 12.05 |
| EDTA disodium dihydrate | 0.015 | 0.018 | 0.020 | 0.023 |
| De-ionized water (DI-water) | 75.1 | 60 | 50 | 40 |

Procedure

The F-1 nanodispersion was first prepared and converted to three anhydrous gels (F-2, F-3 and F-4) containing 40, 50 and 60% water as follows:
  1. Weigh out sesame oil, soy lecithin and cholesterol into a glass flask.
  2. Add ethanol USP.
  3. Rotate the flask to dissolve all solids.
  4. Vacuum dry to remove ethanol to less than 1% by weight.
  5. Add VES (in a 5% stock solution), sucrose, EDTA and DI-water.

6. Add a recombinant human insulin stock solution (HUMULIN® R U100 by Eli Lilly and Co.).
7. Mix to form a primary dispersion.
8. Adjust pH to 6.8 using NaOH/HCl.
9. Homogenize the primary dispersion using a Microfluidics International Corp. Model M-110EH to obtain a nanodispersion. Continue the process until the average particle diameter is about 88 nm as determined by laser light scattering (Malvern Nano Zetasizer).
10. Filter the nanodispersion through a 0.2-micron filter (Millipore Sterflip) in a biosafety hood to sterilize the nanodispersion.
11. Aseptically, remove water using a rotational evaporator to reach water content at 60% to obtain the F-2 gel. Continue the drying process to 50% water for F-3, and 40% for F-4.

The F-2, F-3 and F-4 aqueous gels were one-phase and translucent gels. All satisfied the Acceptable Injectability Criterion. The insulin concentration and integrity were confirmed by an RP-HPLC analysis according to USP.

Example 3

Preparation of Aqueous Gels Containing Recombinant Human Insulin for Basal Insulin Therapy The procedure was directed to preparation of aqueous gels containing recombinant human insulin at 100 IU/mL and 50% water using a soy lecithin (F-1G) and a synthetic phospholipid (F-5G). The insulin was introduced into the process before microfluidization.

| | Compositions (% wt) | | | |
|---|---|---|---|---|
| | F-1G | | F-5G | |
| Component | (Nanodispersion) | (Gel) | (Nanodispersion) | (Gel) |
| Recombinant human insulin | 0.284 | 0.379* | 0.284 | 0.379* |
| Sesame oil | 4 | 8.03 | 4 | 8.03 |
| Phospholipon 90G (PL90G) | 15 | 30.12 | | |
| 1-Palmitoyl-2-Oleoyl-sn-glycero-3-phosphocholine (POPC) | | | 15 | 30.12 |
| Cholesterol | 0.6 | 1.2 | 0.6 | 1.2 |
| Vitamin E succinate (VES) | 0.3 | 0.6 | 0.3 | 0.6 |
| Sucrose | 5 | 10.04 | 5 | 10.04 |
| EDTA disodium dihydrate | 0.011 | 0.015 | 0.011 | 0.015 |
| Histidine | 0.078 | 0.104 | 0.078 | 0.104 |
| De-ionized water (DI-water) | 75.1 | 50 | 75.1 | 50 |

*Equivalent to 100 IU/g

Procedure

The nanodispersions were first prepared and converted to the anhydrous gels following the steps below:
1. Weigh out sesame oil, PL90G or POPC and cholesterol into a glass flask.
2. Add ethanol USP.
3. Rotate the flask to dissolve all solids.
4. Vacuum dry to remove ethanol to less than 1% by weight.
5. Add VES (in a 5% stock solution), sucrose, EDTA, histidine and DI-water.
6. Add recombinant human insulin powder (Incelligent SG by Millipore, 26.4 USP unit/mg)
7. Mix to form a primary dispersion.
8. Adjust pH to 7 using NaOH/HCl.
9. Homogenize the primary dispersion using a Microfluidizer Model M-110EH to obtain a nanoemulsion. Continue the process until the average particle diameter is about 53 nm as determined by laser light scattering (Malvern Nano Zetasizer).
10. Filter the nanodispersion through a 0.2-micron filter in a biosafety hood for sterilization.
11. Aseptically, remove water by a rotational evaporator until the water content is about 50% to obtain an F-1G or F-5G aqueous gel.

The F-1G and F-5G were one-phase, colorless (F-5G) and transparent gels. Both met the Acceptable Injectability Criterion (FIG. 1). Water contents were confirmed by thermogravimetric analysis.

Example 4

Preparation of Recombinant Human Insulin Aqueous Gels Containing Additional Functional Excipients for Basal Insulin Therapy The following compositions were made using the same procedure as described in EXAMPLES 1 to 3 to prepare aqueous gels, but contained recombinant human insulin at 100 IU/mL and water at 50% water. However, a synthetic phospholipid and various other excipients were added in the aqueous phase to increase stability. Sucrose, EDTA disodium dehydrate, M-cresol, phenol, L-histidine, L-cysteine, zinc (as zinc chloride), and/or protamine sulfate were dissolved in the aqueous phase first. The insulin was introduced into the process before the microfluidization step.

| | Compositions | | | |
|---|---|---|---|---|
| % Wt | F-6G | F-7G | F-8G | F-9G |
| Recombinant Human Insulin powder (at 26.4 U/mg) | 0.379 | 0.379 | 0.379 | 0.379 |
| Sesame oil | 8 | 8 | 8 | 8 |
| POPC | 30 | 30 | 30 | 30 |
| Cholesterol | 1.2 | 1.2 | 1.2 | 1.2 |
| VES | 0.6 | 0.6 | 0.6 | 0.6 |
| Sucrose | 10 | 10 | 10 | 10 |
| EDTA disodium dehydrate | 0.1 | | | |
| M-CRESOL | 0.16 | 0.16 | 0.16 | 0.16 |
| Phenol | 0.065 | 0.065 | 0.065 | 0.065 |
| L-Histidine | 0.1 | 0.1 | 0.1 | 0.1 |
| L-cysteine | | | 0.1 | 0.1 |
| Zinc | | | | 0.0025 |
| Protamine sulfate | | | | 0.024 |
| Water DI- | 49.40 | 49.50 | 49.40 | 49.37 |
| Total | 100 | 100 | 100 | 100 |

F-6G, F-7G, F-8G and F-9G were one-phase, colorless and transparent/translucent (or opaque in the case of F-9G) gels. All were readily injectable through a 26 G needle. The insulin concentration and integrity in each gel were confirmed by an RP-HPLC analysis according to the standard USP method.

Example 5

Preparation of Anhydrous Gels Containing HUMULIN® R and HUMULIN® NPH for Basal Insulin Therapy The procedure was directed to preparation of anhydrous gels containing recombinant human insulin (HUMULIN®) and recombinant human insulin zinc/protamine complex (HUMULIN® N, or NPH) at about 100 IU/g. HUMULIN® R or HUMULIN® NPH are insoluble in oil, incompatible with organic solvents and are heat-sensitive. This method allows dissolution or incorporation of these hydrophilic pharmacologically active agents into a sterilized water-free anhydrous gel without using a terminal heat sterilization step in the process.

| Composition (% wt) | | |
| --- | --- | --- |
| Component | S-4 | S-9 |
| HUMULIN® R | 100 IU/mL | / |
| HUMULIN® NPH | / | 100 IU/mL |
| Soy lecithin | 54 | 54 |
| Sesame oil | 40 | 40 |
| Ethanol | 6 | 6 |

A 1 g batch for S-4 or S-9 was prepared as follows:
1. Weigh out sesame oil, soy lecithin and water-for-injection into a plastic tube.
2. Homogenize using a Beadbeater to form a nanodispersion.
3. Pass through a 0.2 micron pore filter.
4. Add HUMULIN® R solution or HUMULIN® NPH suspension to the filtered emulsion. Mix well.
5. Lyophilize the nanodispersion to remove water to less than 1%.
6. Add ethanol.
7. Mix well to obtain an Anhydrous Gel (S-4 and S-9). The S-4 was a one-phase and translucent gel and S-9 was a one-phase opaque gel. Both gels were readily injectable through a 26 G needle. The insulin strengths in these gels were confirmed by HPLC analysis.

Example 6

Preparation a Long-acting Depot Comprising an Anhydrous Gel Containing Buprenorphine Hydrochloride The procedure was directed to preparation of an anhydrous gel containing water-soluble anesthetic buprenorphine hydrochloride. Buprenorphine hydrochloride is insoluble in oil and is heat-sensitive. This method allows a complete dissolution/incorporation of this hydrophilic pharmacologically active agent in a water-free anhydrous gel without the need for a terminal heat sterilization step in the process.

| Composition (% wt) | |
| --- | --- |
| Component | F-27 |
| Buprenorphine HCl | 0.52 |
| 1,2-Dimyristoyl-sn-glycero-3-phosphoglycerol, ammonium/sodium salt (DMPG) | 0.71 |
| Phospholipon 90G | 55.49 |
| Castor oil | 36.99 |
| Benzyl alcohol | 1.00 |
| Ethanol | 5.00 |
| EDTA disodium dehydrate | 0.05 |
| Sodium phosphate monobasic | 0.24 |

Procedure
A 10 g (final gel weight) batch of F-27 was prepared as follows:
1. Weigh out castor oil, lecithin, benzyl alcohol, buprenorphine HCl and DMPG into a plastic bottle. Mix to form an oil phase.
2. Weigh out EDTA, sodium phosphate monobasic and Water-for-Injection, USP (WFI) in a separate container; shake to dissolve all solids and adjust pH to 7 to obtain an aqueous phase. Filter the aqueous phase.
3. Add the aqueous phase to the oil phase. Shake vigorously to form a primary dispersion.
4. Homogenize by sonication to form a nanodispersion.
5. Freeze-dry the nanodispersion to remove water to less than 2%.
6. Add ethanol.
7. Mix well to obtain an Anhydrous Gel (F-27).

F-27 was a one-phase, opaque gel that was readily injectable through a 26 G needle. The buprenorphine strength in this gel was confirmed by HPLC and the water content confirmed using thermogravimetric analysis. The resultant gel is intended as a long-acting depot (e.g., once-a-week dosing) for systemic analgesia or for treatment of narcotic drug abuse.

Example 7

Preparation of an Aqueous Gel Containing Docetaxel

The procedure was directed to preparation of an aqueous gel (F-177) containing a highly water-insoluble drug docetaxel and 50% water using a soy lecithin. Docetaxel was introduced into the process before microfluidization. This docetaxel gel depot is for intra-tumor injection to provide a prolonged anticancer activity.

| Compositions (% wt) | | |
| --- | --- | --- |
| | F-177 | |
| Component | Primary dispersion | Gel |
| Docetaxel trihydrate | 0.600 | 0.811 |
| Miglyol 812 | 4.000 | 5.405 |
| Soybean oil | 4.000 | 5.405 |
| Soy lecithin | 10.000 | 13.514 |
| Cholesterol | 0.6 | 0.811 |
| Vitamin E succinate (VES) | 0.3 | 0.404 |
| Sucrose | 17.5 | 23.649 |
| Water-for-Injection | 67 | 50 |
| 1N NaOH/HCl | adjust pH to 7.6 | |

Procedure
A 500 g (primary dispersion wt) batch was prepared and converted to an aqueous gel as follows:
2. Weigh out docetaxol trihydrate, Miglyol 812, soybean oil, soy lecithin and cholesterol into a glass flask.
3. Add 500 mL ethanol USP 200 proof.
4. Rotate the flask to dissolve all solids at 50° C.
5. Vacuum dry to remove ethanol to less than 2% by weight.
6. Add VES (in a 5% stock solution), sucrose and DI-water.
7. Mix to form a primary dispersion.
8. Adjust pH to 7.6+/−0.2 using NaOH/HCl.
9. Homogenize the primary dispersion using a Microfluidics International Corp. Model M-110EH to obtain a nanodispersion. Continue the process until the average particle diameter is about 100 nm as determined by laser light scattering (Malvern Nano Zetasizer).
10. Filter the nanodispersion through a 0.2-micron pore filter in a biosafety hood to sterilize the nanodispersion.

11. Aseptically, remove water from the nanodispersion using a rotational evaporator until the water content is about 50% to obtain the F-177 aqueous gel.

Example 8

Preparation of a Long-acting Depot Comprising an Anhydrous Gel Containing Lidocaine This procedure was directed to preparation of an anhydrous gel containing the highly water-soluble local anesthetic lidocaine. This method also allows incorporation of the water-soluble (and fat-insoluble) excipients (i.e., EDTA disodium dihydrate and potassium monobasic phosphate, KOH) in the anhydrous gel.

| Composition (% wt) | |
|---|---|
| Component | F-20 |
| Lidocaine | 2 |
| Soy lecithin | 45 |
| Sesame oil | 44 |
| EDTA disodium dehydrate | 0.10 |
| Potassium monobasic phosphate | 0.14 |
| Benzyl alcohol | 1 |
| Ethanol | 4 |
| 1N KOH | pH to 7.0 |

Procedure

A 20 g (final gel weight) batch was prepared as follows:

1. Weigh out lidocaine, sesame oil, soy lecithin and benzyl alcohol into a glass flask.
2. Add ethanol USP 200 proof and rotate the flask to dissolve all.
3. Vacuum dry to remove ethanol to less than 1% by weight.
4. Add $KH_2PO_4$, EDTA and DI-water.
5. Homogenize to form a nanodispersion.
6. Adjust pH to 7.0+/−0.2 using NaOH/HCl.
7. Sterile filter the nanodispersion through a 0.2 micrometer pore filter.
8. Lyophilize the nanodispersion to remove water to less than 2%.
9. Add ethanol.
10. Mix well to obtain an anhydrous Gel (F-20).

The F-20 is a one-phase, slightly yellow and translucent gel that is readily injectable through a 26 G needle.

Example 9

Preparation of an Aqueous Gel Containing Exenatide as a Long-Acting Depot

An aqueous gel depot is prepared to contain about 2 mg/mL exenatide using a composition and method as described in EXAMPLE 3. The resultant gel is a long-acting depot (e.g. once-a-week dosing) of this anti-diabetic drug.

Example 10

Preparation of a Long-acting Depot Comprising an Aqueous Gel Containing Interferon Beta-1a.

An aqueous gel depot is prepared to contain about 35-350 microgram/mL interferon beta-1a using a composition and method as described in EXAMPLE 3 and 4. The resultant gel is a long-acting depot (e.g., once-a-week dosing) and reduced injection site reaction of this anti-viral, antiproliferative and immunomodulatory drug.

Example 11

Preparation of a Long-acting Depot Comprising an Aqueous Gel Containing Heparin

An aqueous gel is prepared to contain about 40-500 microgram/mL enoxaparin sodium (Lovenox) using a composition and method as described in EXAMPLES 3 and 4. The resultant gel is a long-acting depot (e.g. once-a-week dosing) for prophylaxis and treatment of deep vein thrombosis (DVT), ischemic angina and myocardial infarction.

Example 12

Preparation of Long-acting Depot Comprising an Aqueous Gel Containing Epoetin Alpha An aqueous gel depot is prepared to contain about 10-30 K units/mL Epoetin alpha (EPOGEN®) using a composition and method as described in EXAMPLES 3 and 4. The resultant gel is a long-acting depot (e.g., once-a-week dosing) for erythrocytopenia.

Example 13

Preparation of Long-acting Depot Comprising an Anhydrous Gel Containing Growth Hormone An anhydrous gel is prepared to contain about 5-50 mg/mL human growth hormone (somatropin) using a composition and method as described in EXAMPLES 5 and 6. The resultant gel is a long-acting depot (e.g. once-a-week dosing) for growth hormone deficiency in pediatric and adult patients, Turner syndrome and SHOX deficiency.

Example 14

Preparation of Long-acting Depot Comprising an Anhydrous Gel Containing Adalimumab An anhydrous gel depot is prepared to contain 1 to 20% adalimumab (Humira) using a composition and method as described in EXAMPLES 5 and 6. The resultant gel is a long-acting depot (e.g. once-a-week dosing) for treatment of arthritis, psoriasis, ankylosing spondylitis and Crohn's disease.

Example 15

Preparation of a Long-Acting Depot Comprising an Anhydrous Gel Containing Cefazolin, Metronidazole or a Combination Thereof An anhydrous gel depot is prepared to contain about 5 to 20% Cefazolin, 50 mg/mL Metronidazole or a combination thereof using a composition and method as described in EXAMPLES 5 and 6. The resultant gel is a long-acting depot following instillation into surgical wound or injection into the soft tissue near the surgical wound to prevent post surgical infection.

Example 16

Preparation of a Long-acting Depot Comprising an Anhydrous Gel Containing Bupivacaine An anhydrous gel depot is prepared to contain about 40 mg/mL bupivacaine HCl using a composition and method as described in EXAMPLES 5 and 6. The resultant gel is a long-acting depot following instillation into a surgical wound or injection into the soft tissue surrounding the surgical wound to alleviate post surgical pain.

Example 17

Prolonged and Peak-less Pharmacokinetic Profile by an Anhydrous Gel Containing Buprenorphine HCl in Dogs A pharmacokinetic study was conducted where 6 dogs were administered at 0.25 mg/kg dose by subcutaneous or intramuscular injection of the F-27 anhydrous gel depot as described in EXAMPLE 6. Plasma samples were taken and the buprenorphine content analyzed by LC-MS. The results are shown in FIG. 2. The plasma profiles reveal that F-27 depot provided a prolonged in vivo release for at least 5 days with a low initial burst. The prolonged, controlled and essentially peak-less PK profile can be a very desirable feature for drugs where a high $C_{max}$ may cause adverse effects.

Example 18

Prolonged Local Analgesic/Anesthetic Efficacy of Lidocaine from an Anhydrous Gel Prepared According to the Method in Example 8 Following Intracutaneous Injection in Guinea Pigs This study was intended to compare the prolonged local analgesic/anesthetic activity of lidocaine in the F-20 depot formulation to an immediate release solution formulation in guinea pig pinprick pain model. An anhydrous gel (F-20 composition) containing the highly water soluble (and oil insoluble) lidocaine was prepared as described in EXAMPLE 8 and a solution formulation ("Control") was also prepared based on the Lidocaine Solution for Injection, USP. Male guinea pigs between 300~350 grams in body weight were used. The anesthesia/analgesia activity was determined using the intracutaneous wheal pinprick model as described in U.S. Pat. No. 6,045,824 by Kim. On the day preceding the injection, the backs of the animals were clipped. Each animal received a 0.25 mL intracutaneous injection of the lidocaine formulation. The reaction to pinpricks at the site of injection was tested just prior to injection (pre-injection) and at specific time points after the injection. The pinpricks were to be applied first to an area outside the wheal at each time point for positive control. After observing the animals' normal reaction to the pinprick (vocalization response), six pricks were applied inside the wheal and the pricks in which a guinea pig failed to react out of the six were recorded as no-pain responses. The pinpricks were applied in the order of left, center, right, upper, center and lower sections inside the wheal at an interval of 3-5 sec between the pricks. Prior to the injections, all animals were checked for their vocalization reaction to pinpricks as baseline responses. FIG. 3 illustrates the local anesthetic efficacy in percent no-pain response over time for both formulations. The Control animals exhibited 100% analgesic/anesthetic effect at 15 minutes after the injection. However, such effect disappeared quickly with about 50% activity remained after 1 hour and virtually no activity after 4 hours. This is consistent with the short-term anesthetic nature of lidocaine. F-20 provided prolonged local drug activity with about 50% and 40% analgesic activity observed at 12 and 24 hours, respectively, after the injection.

Example 19

Injectability Test for an Aqueous Gel Containing Insulin (F-43)

An aqueous gel coded as F-43 in the following composition was prepared using the method as described in EXAMPLE 2, where the insulin was added after the microfluization step and the average diameter of particles in the nanodispersion was about 40 nm.

| Component | % wt |
| --- | --- |
| Recombinant Human Insulin | 100 IU/g (or about 0.38% wt) |
| POPC | 30 |
| Sesame oil | 8 |
| Cholesterol | 1.2 |
| Vitamin E succinate | 0.6 |
| Sucrose | 2 |
| Glycerin | 1.6 |
| Meta-cresol | 0.027 |
| Phenol | 0.16 |
| Dibasic sodium phosphate anhydrous | 0.065 |
| L-methionine | 0.15 |
| Zinc oxide | 0.378 |
| Protamine base | 0.027 |
| Water for Injection, USP, q.s. | About 56 |

Figure 6:
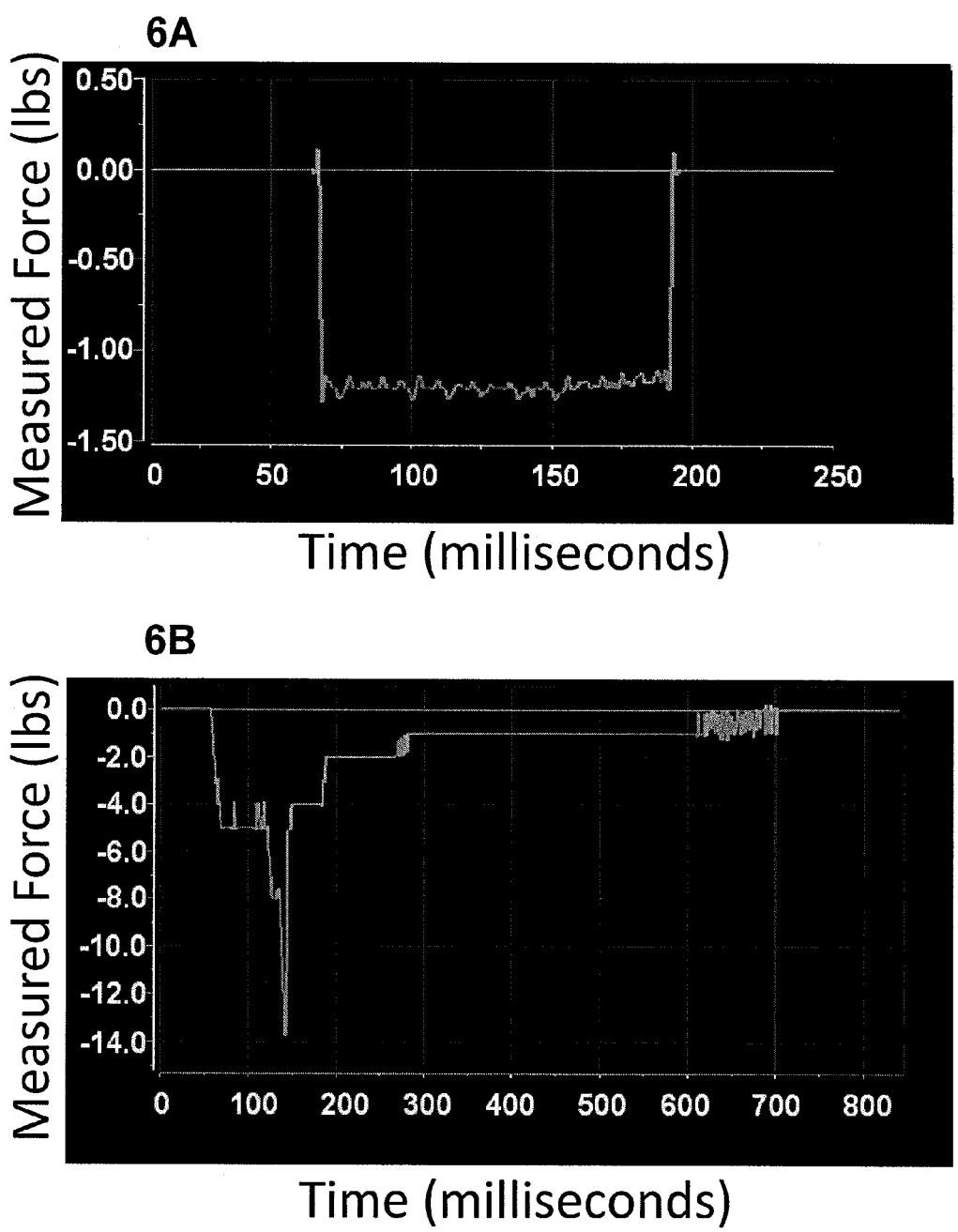
FIG. 6 shows a representative injection force versus time profile for the insulin-containing aqueous gel (F-43) in EXAMPLE 14 (upper panel). The test measured the force necessary to eject the gel from a 1 cc syringe through a 25 G ½ inch long needle at rate of 2 cc/min. For comparison, the force profile for glycerin is shown in the lower panel. With a maximum injection force of less than 1.25 pounds, F-43 can be regarded as very injectable. Even as a gel, it was much easier to inject than the liquid glycerin, which required approximately 8 pounds of force.

F-43 was a translucent one-phase gel. The injectability of F-43 was determined against the Acceptable Injectability Criterion. The maximum force required during the injectability test is recorded as the most relevant measurement parameter for injectability. F-43 was filled into a 1 cc B-D syringe (B-D Luer-Lok Tip, ref 309628) to which a ½" long 25 G needle (EXEL, Hypodermic needle, ref 26403) was attached. The filled syringe was loaded onto a syringe pump to which a force meter (Advanced Precision Instrument Model HP-500) was attached against the plunger end to measure to force applied to extrude the syringe contents. The syringe pump was set at 2 cc/min speed and 0.4 mL extrusion volume. The force was recorded in pounds. In the "push" mode, the force is recorded as negative. A representative injection force versus time profile for F-43 is shown in FIG. 6 (upper panel). For comparison, the force profile from the same composition as F-43, but prepared by one-step vigorous homogenization of all the components together ("Same composition by other method"). With a maximal injection force of less than 1.5 pounds, F-43 is regarded as highly injectable and meeting the Acceptable Injectability Criterion. It is compared very favorably to "Same composition by other method", which required a maximum force of about 14 pounds in the evaluation. F-43 was also filled into a insulin pen cartridge (Eli Lily HUMULIN® N Cartridge) and injected using a pen injector device (HUMAPEN LUXURA® by Eli Lilly and company). At a dialed injection volume of 20 U, the injected volume in repeated injections was found to be accurate and precise. F-43 is well suited for pen injectors.

Example 20

Preparation of a Long-acting Depot Comprising an Anhydrous Gel Containing Prednisone An anhydrous gel depot is prepared to contain about 40 mg/mL prednisone using a composition comprising 50% soy lecithin, 40% sesame oil, and 6% ethanol using the method as follows:
a. Mix soy lecithin, water and sesame oil to form a primary dispersion.
b. Remove water by lyophilization to less than 1%.
c. Add ethanol.
d. Mixing to obtain an anhydrous gel.
e. Pass the gel though a 0.45-micron filter for sterilization.
The resultant gel is a long-acting depot for treatment of inflammation.

Example 21

Preparation of an Anhydrous Gel Containing Ibuprofen

An anhydrous gel depot is prepared to contain about 4 to 20% wt ibuprofen using a composition and method as described in EXAMPLE 20. The resultant gel is a long-acting depot for treatment of inflammation and pain.

Example 22

Preparation of a Long-Acting Depot Comprising an Anhydrous Gel Containing Clotrimazole An anhydrous gel depot is prepared to contain about 40 mg/mL clotrimazole using a composition and method as described in EXAMPLE 20. The resultant gel is a long-acting depot for treatment of fungal infection.

Example 23

Preparation of a Long-acting Depot Comprising an Anhydrous Gel Containing Risperidone An anhydrous gel depot is prepared to contain about 40 mg/mL Risperidone using a composition and method as described in EXAMPLE 6. The resultant gel is a long-acting depot for treatment of psychological disorder.

Example 24

Preparation of a Long-acting Depot Comprising an Anhydrous Gel Containing Tamoxifen Citrate An anhydrous gel depot is prepared to contain about 51 mg/mL Tamoxifen Citrate using a composition and method as described in EXAMPLE 6. The resultant gel is a long-acting depot for treatment of cancer.

Example 25

Preparation of a Long-Acting Depot Comprising an Anhydrous Gel Containing Diazepam An anhydrous gel depot is prepared to contain about 40 mg/mL Diazepam using a composition and method as described in EXAMPLE 20. The resultant gel is a long-acting depot for treatment of anxiety.

Example 26

Preparation of a Long-Acting Depot Comprising an Anhydrous Gel Containing Docetaxel An anhydrous gel depot is prepared to contain about 40 mg/mL Docetaxel using a composition and method as described in EXAMPLE 20. The resultant gel is a long-acting depot for treatment of cancer.

Example 27

Prolonged (24 Hr) Insulin Pharmacodynamic Effect by Aqueous Gels Containing Insulin (F-43 and F-44)

The objective of this study was to evaluate two aqueous gel PG compositions containing recombinant human insulin F-43 (as in EXAMPLE 19) and F-44 in the streptozotosin (STZ)-induced type-I diabetic Sprague Dawley rat model. This study compared the pharmacodynamic or PD (i.e., blood glucose level versus time) profiles for two PG depots with the PD profiles for two marketed basal insulin drugs (Insulin NPH or HUMULIN® N and LANTUS®) all at about 100 IU/mL strength. F-44 was prepared as an Aqueous gel comprising 100 IU/mL recombinant human insulin, 50% POPC, zinc, protamine, phenol, m-cresol, glycerol, sodium phosphate and about 40% water using the method as described in EXAMPLE 2, wherein the insulin was added after the microfluization step.

Type I diabetes in Sprague Dawley rats was induced by intravenous injection of STZ. Twenty-four (24) STZ-treated rats were randomly divided into 4 groups. Small blood samples were taken from the lateral tail vein of each animal and the blood glucose levels were measured using a glucometer. The animals were successfully assigned to treatment groups such that there were no significant differences between groups in body weight or blood glucose level as measured by one-way ANOVA (P>0.05). The animals were fasted for at least 12 hours and then the blood glucose levels were measured just prior to administration of the test articles. The four formulations were administered subcutaneously at 20 IU/kg. Blood glucose levels were measured at −0.25, 0.25, 5, 1, 2, 4, 6, 8 16 and 24 hr post-insulin administration in Experiment 1. Blood glucose levels were focused on the late time points for experiment 2 at −0.25, 1, 2, 12, 14, 16, 18, 20, 22, 24 and 36 hr post-insulin administration. The blood glucose data versus time was graphed and the data was analyzed with a two-way ANOVA with Bonferroni's post hoc test to evaluate pair wise comparisons between test formulations at each measurement time point. Experiment 1 indicated that treatment with PG formulated insulin resulted in 24 hours of good glycemic control (blood glucose level maintained between 50 and 130 mg/dl) for F-44 and about 18 hours for F-43 (FIG. 7). The duration of glycemic control ranking was: F-44 (.gtoreq.24 hr)>F-43 (18 hr)>HUMULIN® N (.about. 12-24 hr)>LANTUS® (12 hr).

All four tested formulations exhibited similar onset of action by achieving glycemic control within about 1 hour after the subcutaneous injection. F-44 exhibited significantly lower blood glucose at later time points (between 16 to 24 hrs) compared to the three other formulas. There was no significant blood glucose level difference detected at early time points. In addition, F-43 was able to keep blood glucose controlled for up to 18 hours after dosing. A repeated study (Experiment 2) also confirmed the findings from Experiment 1; that is, F-44 can control blood glucose up to 24 hrs and F-43 can maintain low blood glucose level (<130 mg/dl) for at least 18 hrs. In comparison, LANTUS®-treated rats achieved glycemic control for only 12 hours. HUMULIN® N showed the highest animal-to-animal variability in blood glucose level.

Example 28

Prolonged (24 hr) and Peak-Less Pharmacokinetic Profile of Human Insulin Following Subcutaneous Injection of an Aqueous Gel Containing Human Insulin (F-43)

The objective of this study was to evaluate F-43 (EX-AMPLES 19 and 26) in STZ-induced type-I diabetes conscious Sprague Dawley rats by comparing PK profiles (plasma insulin versus time) with a marketed insulin drug (NPH Insulin/HUMULIN® N).

Type I diabetes in Sprague Dawley rats was induced by intravenous injection of STZ. Eight (8) rats (all having STZ-induced type I diabetes, Sprague Dawley) were placed into two treatment groups (F-43 and NPH). Small amounts of blood samples were taken from the lateral tail vein of each animal and the blood glucose levels were measured using a glucometer. 0.3 ml of whole blood was taken from jugular vein and placed in EDTA-coated tubes for plasma separation. The concentrations of human insulin in plasma were measured using human insulin ELISA kit and RIA kits. The animals were assigned to treatment groups such that there were no significant differences between groups in body weight or blood glucose level as measured by two-tailed student t test (P>0.05). The animals were fasted for at least 12 hours and then the blood glucose levels were measured just prior to administration of the test formula.

The two formulations were administered subcutaneously at 20 IU/kg. Blood glucose levels were measured at pre, 1, 2, 4, 6, 8, 16, 20 and 24 hr post-insulin administration. Blood glucose and insulin levels versus time was graphed and the data was analyzed with a two-way ANOVA with Bonferroni's post hoc test to evaluate pair wise comparisons between test formulations at each measurement time point. The data indicated that treatment resulted in about 24 hr glycemic control (blood glucose level maintained at below 130 mg/dl) by F-43 or about 16 hr by NPH/HUMULIN® N (FIG. 8 lower panel). The rats treated with F-43 exhibited a steady and prolonged plasma insulin concentration profile between about 300 to 400 .mu.IU/mL by the ELISA or between 250 and 400 .mu.IU/mL by the RIA method for about 24 hours, whereas the NPH-treated rats showed continuous drop in plasma insulin concentration, which diminished at about 24 hours. Moreover, treatment with F-43 resulted in a "peakless" PK profile (FIG. 8 upper panel). Both tested formulations exhibited similar onset of action, achieving glycemic control within about the first hour after the SC administration.

Example 29

Single-Phase and Content Uniformity Study of F-43

The objective of this study was to demonstrate the single-phase stability and the concentration uniformity of insulin in F-43 (as in EXAMPLE 19) as studied using an insulin pen-injector.
Procedure:
A) Day 1:
1. Insert one pen injector cartridge vial filled with F-43 or HUMULIN® N(NPH) into a pen injector (HU-MAPEN LUXURA® by Eli Lilly and Company).
2. Roll the pen back and forth 10 times and turn the pen up and down 10 times to mix the content in the cartridge vial.
3. Attach a Novofine 28G×12 mm needle.
4. Turn dose knob to 20 units and inject the content into a small plastic vial, record the weight of the content injected. Repeat the injection 9 times.

Determine concentration of insulin in each injection by HPLC analysis.
B) Day 2, 7 and 14:
Repeat the Day 1 procedure except Step 2.
Results

|  | Insulin IU/g | | | Insulin IU/g | | | |
| --- | --- | --- | --- | --- | --- | --- | --- |
| Sample ID | Day 1 | Day 2 | Sample ID | Day 1 | Day 2 | Day 7 | Day 14 |
| HUMULIN® N, Inj #1 | 91.8 | 296.9 | F43, Inj #1 | 104.1 | 100.6 | 113.8 | 97.1 |
| HUMULIN® N, Inj #2 | 95.4 | 265.5 | F43, Inj #2 | 105.1 | 98.7 | 110.9 | 96 |
| HUMULIN® N, Inj #3 | 98.8 | 220.2 | F43, Inj #3 | 104.1 | 100.2 | 97.6 | 95.9 |
| HUMULIN® N, Inj #4 | 96.4 | 167.1 | F43, Inj #4 | 101.8 | 102.8 | 98.1 | 97.3 |
| HUMULIN® N, Inj #5 | 101.9 | 110.4 | F43, Inj #5 | 100.9 | 104.9 | 96.6 | 97 |
| HUMULIN® N, Inj #6 | 111.6 | 74.9 | F43, Inj #6 | 99.6 | 102.5 | 95.4 | 96.7 |
| HUMULIN® N, Inj #7 | 109.4 | 51.4 | F43, Inj #7 | 102.6 | 103.7 | 98.2 | 96.6 |
| HUMULIN® N, Inj #8 | 110 | 26.1 | F43, Inj #8 | 103.1 | 103.5 | 100.1 | 95.9 |
| HUMULIN® N, Inj #9 | 89.5 | 15.8 | F43, Inj #9 | 103.4 | 104.4 | 97.4 | 95.6 |
| HUMULIN® N, Inj #10 | 90.6 | 21.3 | F43, Inj #10 | 103.7 | 104.2 | 97.5 | 97.7 |
| Avg | 99.5 | 124.95 | Avg | 102.84 | 102.55 | 100.57 | 96.56 |
| RSD | 8.3 | 105.8 | RSD | 1.7 | 2.1 | 6.4 | 0.7 |
| CV | 8.4 | 84.7 | CV | 1.6 | 2.0 | 6.3 | 0.7 |

Conclusion: F-43 exhibited good content uniformity over time even without implementing the pre-dosing mixing ritual that is required for HUMULIN® N. HUMULIN® N on the other hand showed high injection-to-injection variability between about 8% and 85%. A separate study also shown that the F-43 remained uniform in its insulin content after centrifugation at no less than 1000 RPM for no less than 5 minutes.

Example 30

Preparation of an Aqueous Gel Containing Insulin Determir for Basal Insulin Therapy The Example is directed to preparation of an aqueous gel containing insulin detemir, which is an insulin analog originally created by Novo Nordisk. An aqueous gel is prepared in a composition similar to F-43 as in EXAMPLE 19, wherein the Recombinant Human Insulin is replaced with 100 to 400 IU/mL insulin determir and the other components include POPC, sesame oil, sucrose, m-cresol, phenol, methionine and water. The method described in EXAMPLE 2 is used wherein insulin determir, is added before or after the nanodispersion is formed. This composition is intended for basal insulin therapy to provide glycemic control for 24 hours or longer.

Example 31

Preparation of an Aqueous Gel Containing NPH Insulin for Basal Insulin Therapy The Example is directed to preparation of an aqueous gel containing NPH Insulin, which is also known as insulin isophane. An aqueous gel is prepared in a composition similar to F-43 as in EXAMPLE 19, wherein the Recombinant Human Insulin is replaced with 100 to 400 IU/mL NPH insulin and the other components include POPC, sesame oil, sucrose, glycerol, m-cresol, phenol, methionine, sodium phosphate and water. The method described in EXAMPLE 2 is used wherein NPH is added after the nanodispersion is formed. This composition is intended for basal insulin therapy to provide glycemic control for 24 hours or longer.

Example 32

Preparation of an Aqueous Gel Containing botulism toxin type A for an Aesthetic Medicine Indication The Example is directed to preparation of an aqueous gel in a composition similar to F-43 as in EXAMPLE 19, wherein the Recombinant Human Insulin is replaced with 100 units/g (about 0.5 nanograms/g) of BOTOX® or purified botulinum toxin type A. The method described in EXAMPLE 2 is used wherein purified botulinum toxin type A is added before or after the nanodispersion is formed. This composition is intended for the temporary improvement in the appearance of moderate to severe glabellar lines associated with corrugator and/or procerus muscle activity in adult patients years of age.

Example 33

PG Structural Characterization by Small Angle X-Ray Scattering (SAXS)

Figure 10:
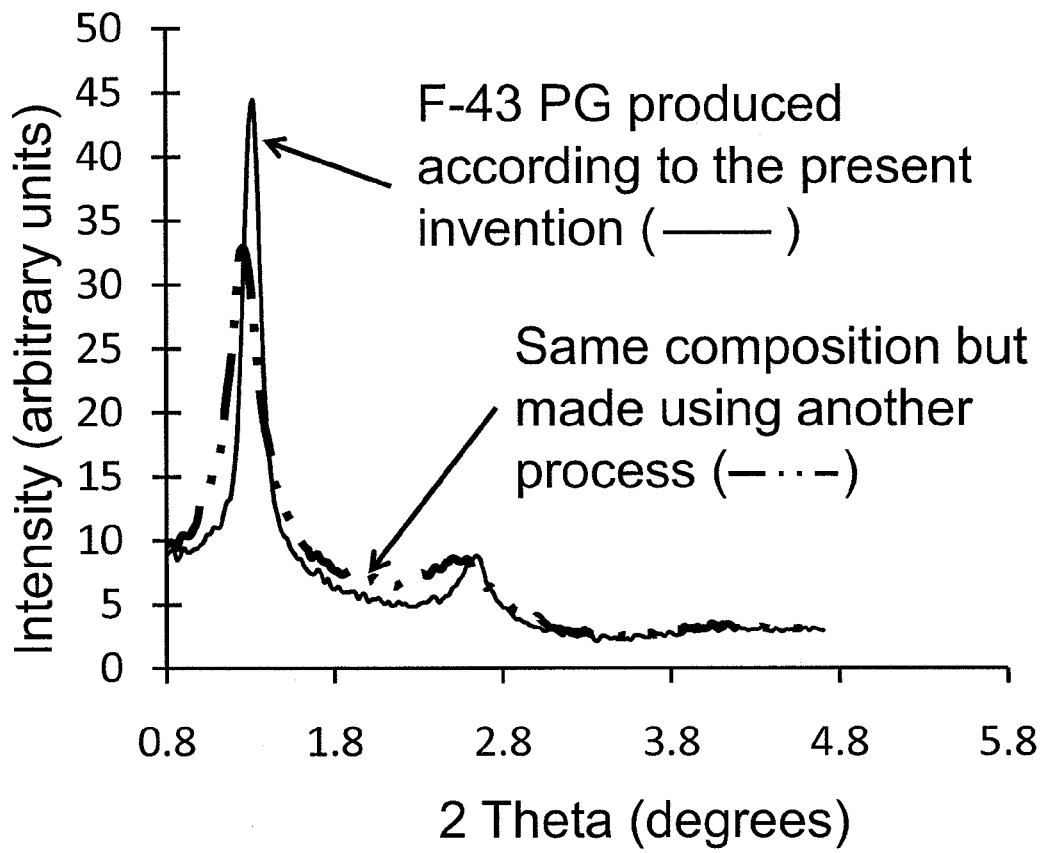
FIG. 10 shows SAXS diffractograms for F-43 PG prepared according to the method disclosed in the present invention ("F-43 PG according to the present invention") and the same composition as F-43, but prepared by direct mixing ("Same composition by other method").

Small-angle X-ray scattering (SAXS) is an analytical technique that provides nanoscale information of particle or lattice systems in terms of such parameters as averaged particle sizes, shapes, distribution, and spacing etc. This information can be used to quantitative determine the structural organization of materials such as gels. For a comparison of two gel samples, SAXS can show either differences in structures (particle size, stacking etc.) or the degree of molecular order which differentiates an ordered structure from a less ordered or random structures. SAXS data is usually presented in diffractograms (FIG. 10). Peaks observed in a SAXS diffractogram is measured for scattering angle (on X-axis) which corresponds to lattice spacing in an ordered structure and the scattering intensity (peak height) and sharpness, which relate to degree of order.

Two gel samples containing insulin were prepared and tested by SAXS. The first one is an aqueous gel of the present invention in the F-43 composition as described in EXAMPLE 19 and the other one contains the same components as in F-43 but was prepared by combining all components and homogenizing extensively using a high-speed mixer (Mini-beadbeater). The second composition ("F-43 by Direct Mixing") was not prepared using the invention method The SAXS data were collected in a helium chamber using a Bruker M18XHF rotating anode generator operating at 50 kV and 50 mA supplying a Cu Kα(λ=1.541838 Å) radiation beam that was collimated using a pinhole collimator. Kβ radiation was filtered out with a Ni filter. A Highstar multiwire detector was used to collect the data. The samples were loaded without modification into 0.9 mm borosilicate glass capillaries and sealed with epoxy. The samples were mounted in the He chamber on an automated goniometer at sample to detector distance of 64.55 cm. To prevent scatter from air He gas was purged into the chamber for 1 hour and then each sample was collected for 7200 seconds. The data were smoothed and integrated over the 360° χ circle from 0.8 to 4.7° 2θ in 0.02 degree widths.

FIG. 10 shows diffractograms for both F-43 and F-43 by Direct Mixing. Each sample showed two peaks. Provided below are the lattice d spacing (d(Å)) calculated by assuming n=1 for the Bragg equation (nλ=2d sin(θ)) and degree of order or size of "crystalline" domains based on the Scherrer equation:

$$\left(\tau = \frac{K\lambda}{\beta\cos\theta}\right)$$

| Sample | Peak # | d (Å) | Degree of Order (Scherrer Crystalline domain size (nm)) |
|---|---|---|---|
| F-43 by Direct Mixing | 1 | 70.00 | 42.3(3) |
|  | 2 | 34.70 | 16.0(3) |
| F-43 | 1 | 67.38 | 81.3(5) |
|  | 2 | 33.61 | 33.4(5) |

The SAXS data suggested that both samples have two phases (peaks). Compared to F43 by Direct Mixing, F-43 exhibits somewhat different lattice d spacing in phase 1 (peak 1) and a greatly increased Scherrer Crystalline domain size or degree of order in both phases. This can be also seen in the sharpening of the peaks in F-43 as compared to F-43 by Direct Mixing.

This SAXS study shows that F-43 PG material produced by the method of this invention has an ordered structure and higher degree of structural order than the same composition prepared another method. The ordered structure found in the PG of the present invention is consistent to the stacked balloon model as depicted in FIG. 9 and is believed to be the reason for the surprisingly good injectability of the PGs.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group. Other embodiments are set forth within the following claims.

What is claimed is:

1. An nanoemulsion based injectable one-phase gel composition, comprising:
   about 30% to about 60% by weight of phospholipid based on the total weight of the gel, wherein the phospholipid is a member selected from the group consisting of a lecithin, phosphatidylcholine or a mixture thereof;
   0.1% to 65% by weight based on the total weight of the gel;
   10% to 50% by weight of an oil based on the total weight of the gel, wherein the phospholipid comprising particles are stacked together and have an average particle size of about 30 nm to about 100 nm in diameter;
   and wherein the composition has an increased degree of order as shown by an increase in the Scherrer crystalline domain size over a composition containing the same quantities of the same components but prepared by a process without forming a nanodispersion and the discrete phospholipid particles; is extrudable or injectable through a 25 G, ½ inch long needle from a 1 cc syringe at an extrusion rate of 2 cc/min by an applied force of no more than 12 pounds.

2. The gel composition of claim 1, further comprising a pharmacologically active agent having concentration of no more than 20% by weight of the final gel composition.

3. The gel composition of claim 2, wherein the pharmacologically active agent is a heat-sensitive pharmacologically active agent.

4. The gel composition of claim 2, wherein the pharmacologically active agent is a protein or peptide.

5. The gel composition of claim 2, wherein the pharmacologically active agent is a member selected from the group consisting of an insulin, an insulin analog, a crystalline insulin with zinc and/or protamine, an NPH insulin, and a combination thereof.

6. The gel composition of claim 5, wherein the phospholipid comprises 30% to 40% by weight based on the total weight of the gel.

7. The gel composition of claim 1, wherein the phospholipid is a lecithin.

8. The gel composition of claim 1, wherein the oil is selected from the group consisting of a synthetic oil, a vegetable oil, a medium chain oil, ethyl oleate, fatty acid, vitamin E, vitamin E succinate, cholesterol, or a mixture thereof.

9. The gel composition of claim 1, further comprising one or more sugars selected from the group consisting of sucrose, dextrose, lactose, glucose, trehalose, maltose, mannitol, sorbitol, glycerol, amylose, starch, amylopectin, or a mixture thereof.

10. The gel composition of claim 1, further comprising one or more non-aqueous solvents selected from the group consisting of ethanol, propylene glycol, glycerol, sorbitol, polyethylene glycol, ethyl oleate, or a mixture thereof.

11. The gel composition of claim 1, further comprising a functional pharmaceutical excipient selected from the group consisting of an acidifying agent, an alkalizing agent, a pH buffering agent, a metal ion chelator, an antioxidant, a preservative, a tonicity/osmotic pressure modifier, a condensing agent, a solubilizing agent, or a mixture thereof.

12. The gel composition of claim 1, where the gel composition has a small-angle X-ray scattering diffractogram of FIG. 10 and a lattice d spacing of 67 Å and 33 Å.

13. The gel composition of claim 1, wherein the gel has an increase in the Scherrer crystalline domain size over a composition containing the same quantities of the same components but prepared by a process without forming a nanodispersion and the discrete phospholipid particles having a diameter of 30-100nm; and (2) a small-angle X-ray scattering diffractogram of FIG. 10 and a lattice d spacing of 67 Å and 33 Å.

14. An injectable one-phase gel composition, comprising about 30% to about 60% by weight of phospholipid, wherein the phospholipid is a member selected from the group consisting of a lecithin, phosphatidylcholine or a mixture thereof based on the total weight of the gel;
   10% to 50% by weight of an oil based on the total weight of the gel; and
   0.1% to 65% by weight water based on the total weight of the gel, wherein said composition is prepared by a process comprising:
   i mixing one or more phospholipid(s) and water to form a primary dispersion;
   ii homogenizing the primary dispersion to form a nanodispersion with an average particle size of about 30 nm to about 100 nm in diameter;
   iii passing the nanodispersion through a filter; and
   iv removing the excessive water to obtain a one-phase gel composition comprising (a) discrete phospholipid particles that are stacked together and have an average particle size of about 30 nm to about 100 nm in diameter; (b) an increased degree of order as shown by an increase in the Scherrer crystalline domain size over a composition containing the same quantities of the same components but prepared by a process without forming a nanodispersion and the discrete phospholipid particles of (a); and (c) is extrudable or injectable through a 25 G ½ inch long needle from a 1 cc syringe at an extrusion rate of 2 cc/min by an applied force of no more than 12 pounds.

* * * * *